United States Patent
Buscemi et al.

(10) Patent No.: US 11,497,931 B2
(45) Date of Patent: Nov. 15, 2022

(54) LENS WITH ASYMMETRIC PROJECTION TO TREAT ASTIGMATISM

(71) Applicant: ACUCELA INC., Seattle, WA (US)

(72) Inventors: Philip M. Buscemi, Mount Pleasant, SC (US); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/304,666

(22) Filed: Jun. 24, 2021

(65) Prior Publication Data
US 2021/0379399 A1    Dec. 9, 2021

Related U.S. Application Data

(63) Continuation of application No. PCT/US2021/036097, filed on Jun. 7, 2021.
(Continued)

(51) Int. Cl.
*A61N 5/06* (2006.01)

(52) U.S. Cl.
CPC .... *A61N 5/0622* (2013.01); *A61N 2005/0626* (2013.01); *A61N 2005/0648* (2013.01)

(58) Field of Classification Search
CPC ...... A61N 5/0622; A61N 5/0613; A61N 5/06; A61N 2005/0648; A61N 2005/0626; A61N 2005/0632
(Continued)

(56) References Cited

U.S. PATENT DOCUMENTS

| 6,516,808 B2 | 2/2003 | Schulman |
|---|---|---|
| 7,018,040 B2 | 3/2006 | Blum |

(Continued)

FOREIGN PATENT DOCUMENTS

| EP | 3153139 | 4/2017 |
|---|---|---|
| EP | 3413116 | 12/2018 |

(Continued)

OTHER PUBLICATIONS

Srinivasan, S., "Ocular axes and angles: Time for better understanding," J. Cataract Refract. Surg., 42:351-352 (Mar. 2016).
(Continued)

*Primary Examiner* — John R Downey
(74) *Attorney, Agent, or Firm* — Fisherbroyles LLP; John Shimmick

(57) ABSTRACT

A stimulus is configured to treat astigmatism with changes in retinal thickness, independently of, or in combination with, treatment for myopia. In some embodiments, a stimulus pattern is arranged with respect to an astigmatic axis of the eye to decrease ocular growth in relation to the astigmatic axis. In some embodiments, the apparatus is configured to direct light to regions of retina outside the macula in relation to the astigmatic axis of the eye. In some embodiments, the intensity is modulated to provide the effect. A lens, such as a contact lens or spectacle lens may be configured with a plurality of light sources, such as projection units having a light source and focusing optics that work together to project anteriorly or posteriorly defocused images onto the retina at locations eccentric to the fovea.

19 Claims, 11 Drawing Sheets

Related U.S. Application Data

(60) Provisional application No. 63/036,170, filed on Jun. 8, 2020.

(58) Field of Classification Search
USPC .................................. 606/4–6; 607/88–89
See application file for complete search history.

(56) References Cited

U.S. PATENT DOCUMENTS

| | | |
|---|---|---|
| 8,246,167 B2 | 8/2012 | Legerton |
| 8,432,124 B2 | 4/2013 | Foster |
| 8,662,664 B2 * | 3/2014 | Artal Soriano ........ G02C 7/041 351/159.41 |
| 8,857,983 B2 | 10/2014 | Pugh |
| 9,345,813 B2 | 5/2016 | Hogg |
| 9,763,827 B2 | 9/2017 | Kelleher |
| 9,885,884 B2 | 2/2018 | Drobe |
| 9,918,894 B2 | 3/2018 | Lam |
| RE47,006 E | 8/2018 | Ho |
| 10,133,092 B2 | 11/2018 | Tsubota |
| 10,146,067 B2 | 12/2018 | Tsai |
| 10,231,897 B2 | 3/2019 | Tse |
| 10,268,050 B2 | 4/2019 | To |
| 10,288,909 B1 | 5/2019 | Youssef |
| 10,788,686 B2 | 9/2020 | Tsai |
| 10,884,264 B2 | 1/2021 | Hones |
| 10,921,612 B2 | 2/2021 | Zhou |
| 10,993,515 B1 | 5/2021 | Kim |
| 11,000,186 B2 | 5/2021 | Linder |
| 11,163,166 B1 | 11/2021 | Ebert |
| 11,187,921 B2 | 11/2021 | Zhou |
| 11,281,022 B2 | 3/2022 | Buscemi |
| 11,320,674 B2 | 5/2022 | Kubota |
| 2002/0186345 A1 | 12/2002 | Duppstadt |
| 2003/0011745 A1 | 1/2003 | Molebny |
| 2004/0237971 A1 | 12/2004 | Radhakrishnan |
| 2004/0246441 A1 | 12/2004 | Stark |
| 2004/0257529 A1 | 12/2004 | Thomas |
| 2006/0082729 A1 | 4/2006 | To |
| 2007/0002452 A1 | 1/2007 | Munro |
| 2007/0076217 A1 | 4/2007 | Baker |
| 2007/0115431 A1 | 5/2007 | Smith, III |
| 2007/0127349 A1 | 6/2007 | Hotta |
| 2008/0291391 A1 | 11/2008 | Meyers |
| 2008/0309882 A1 | 12/2008 | Thorn |
| 2009/0002631 A1 | 1/2009 | Campbell |
| 2009/0187242 A1 | 7/2009 | Weeber |
| 2009/0204207 A1 | 8/2009 | Blum |
| 2010/0076417 A1 | 3/2010 | Suckewer |
| 2010/0296058 A1 | 11/2010 | Ho |
| 2011/0085129 A1 * | 4/2011 | Legerton ................. G02C 7/04 351/159.16 |
| 2011/0153012 A1 * | 6/2011 | Legerton ................. G02C 7/04 351/159.23 |
| 2011/0157554 A1 | 6/2011 | Kawai |
| 2011/0202114 A1 | 8/2011 | Kessel |
| 2012/0062836 A1 | 3/2012 | Tse |
| 2012/0199995 A1 | 8/2012 | Pugh |
| 2012/0206485 A1 | 8/2012 | Osterhout |
| 2012/0212399 A1 | 8/2012 | Border |
| 2012/0215291 A1 | 8/2012 | Pugh |
| 2013/0027655 A1 | 1/2013 | Blum |
| 2013/0278887 A1 * | 10/2013 | Legerton ............... A61B 3/0008 351/158 |
| 2014/0039048 A1 | 2/2014 | Bavik |
| 2014/0039361 A1 | 2/2014 | Siu |
| 2014/0194773 A1 | 7/2014 | Pletcher |
| 2014/0218647 A1 | 8/2014 | Blum |
| 2014/0240665 A1 | 8/2014 | Pugh |
| 2014/0268029 A1 | 9/2014 | Pugh |
| 2014/0277291 A1 | 9/2014 | Pugh |
| 2014/0379054 A1 | 12/2014 | Cooper |
| 2015/0057701 A1 | 2/2015 | Kelleher |
| 2015/0109574 A1 | 4/2015 | Tse |
| 2015/0160477 A1 | 6/2015 | Dai |
| 2015/0241706 A1 | 8/2015 | Schowengerdt |
| 2016/0056498 A1 | 2/2016 | Flitsch |
| 2016/0067037 A1 | 3/2016 | Rosen |
| 2016/0091737 A1 | 3/2016 | Kim |
| 2016/0143801 A1 | 5/2016 | Lam |
| 2016/0158486 A1 * | 6/2016 | Colbaugh ............ A61N 5/0618 607/88 |
| 2016/0212404 A1 | 7/2016 | Maiello |
| 2016/0270656 A1 * | 9/2016 | Samec .................. A61B 3/063 |
| 2016/0377884 A1 * | 12/2016 | Lau ....................... G02C 7/022 351/159.05 |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0078623 A1 | 3/2017 | Hilkes |
| 2017/0097519 A1 | 4/2017 | Lee |
| 2017/0184875 A1 | 6/2017 | Newman |
| 2017/0229730 A1 | 8/2017 | Flitsch |
| 2017/0236255 A1 | 8/2017 | Wetzstein |
| 2017/0270636 A1 | 9/2017 | Shtukater |
| 2017/0276963 A1 | 9/2017 | Brennan |
| 2017/0307779 A1 | 10/2017 | Marullo |
| 2018/0017810 A1 | 1/2018 | Wu |
| 2018/0017814 A1 * | 1/2018 | Tuan ...................... G02C 11/10 |
| 2018/0052319 A1 | 2/2018 | McCabe |
| 2018/0055351 A1 | 3/2018 | Yates |
| 2018/0074322 A1 | 3/2018 | Rousseau |
| 2018/0090958 A1 | 3/2018 | Steger |
| 2018/0092738 A1 | 4/2018 | Tai |
| 2018/0136486 A1 | 5/2018 | MacNamara |
| 2018/0161231 A1 | 6/2018 | Tse |
| 2018/0173010 A1 | 6/2018 | Harant |
| 2018/0188556 A1 | 7/2018 | Portney |
| 2018/0221140 A1 | 8/2018 | Rosen |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1 | 1/2019 | Neitz |
| 2019/0038123 A1 | 2/2019 | Linder |
| 2019/0049730 A1 | 2/2019 | Miller |
| 2019/0076241 A1 | 3/2019 | Alarcon Heredia |
| 2019/0107734 A1 | 4/2019 | Lee |
| 2019/0113757 A1 | 4/2019 | Van Heugten |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250432 A1 | 8/2019 | Kim |
| 2019/0314147 A1 | 10/2019 | Blum |
| 2020/0033637 A1 | 1/2020 | Jamshidi |
| 2020/0089023 A1 | 3/2020 | Zhou |
| 2020/0110265 A1 | 4/2020 | Serdarevic |
| 2020/0133024 A1 | 4/2020 | Paune Fabre |
| 2020/0142219 A1 | 5/2020 | Rousseau |
| 2020/0183169 A1 | 6/2020 | Peng |
| 2020/0360184 A1 | 11/2020 | Xiao |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0263336 A1 | 8/2021 | Gupta |
| 2021/0298440 A1 | 9/2021 | Kim |
| 2021/0356767 A1 | 11/2021 | Kubota |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |

FOREIGN PATENT DOCUMENTS

| | | |
|---|---|---|
| KR | 20180038359 | 4/2018 |
| KR | 20180038359 A | 4/2018 |
| WO | 2009074638 | 6/2009 |
| WO | 2009074638 A3 | 6/2009 |
| WO | 2009121810 | 10/2009 |

(56) References Cited

FOREIGN PATENT DOCUMENTS

| | | |
|---|---|---|
| WO | 2010043599 | 4/2010 |
| WO | 2011089042 | 7/2011 |
| WO | 2012136470 | 10/2012 |
| WO | 2013087518 | 6/2013 |
| WO | 2013158418 | 10/2013 |
| WO | 2014033035 | 3/2014 |
| WO | 2014191460 | 12/2014 |
| WO | 2015063097 | 5/2015 |
| WO | 2015186723 | 12/2015 |
| WO | 2017094886 | 6/2017 |
| WO | 2017097708 | 6/2017 |
| WO | 2018014712 | 1/2018 |
| WO | 2018014960 | 1/2018 |
| WO | 2018085576 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |
| WO | 2021056018 | 3/2021 |
| WO | 2021168481 | 8/2021 |
| WO | 2021231684 | 11/2021 |
| WO | 2021252318 | 12/2021 |
| WO | 2021252319 | 12/2021 |
| WO | 2021252320 | 12/2021 |

OTHER PUBLICATIONS

Torii, Hidemasa, et al., "Violet Light Exposure Can Be a Preventive Strategy Against Myopia Progression," EBioMedicine 15:210-219 (2017).
U.S. Appl. No. 17/302,479, filed May 4, 2021 (60 pages).
U.S. Appl. No. 17/302,827, filed May 13, 2021 (52 pages).
U.S. Appl. No. 17/303,889, filed Jun. 9, 2021 (69 pages).
U.S. Appl. No. 17/304,630, filed Jun. 23, 2021 (68 pages).
U.S. Appl. No. 17/304,691, filed Jun. 24, 2021 (88 pages).
Wallman, Josh, et al., "Homeostasis of Eye Growth and the Question of Myopia," Neuron, 43:447-468 (2004).
Wolffsohn, James A., et al., "Impact of Soft Contact Lens Edge Design and Midperipheral Lens Shape on the Epithelium and Its Indentation With Lens Mobility," IOVS, 54(9):6190-6196 (2013).
Adler, Daniel, et al., "The possible effect of under correction on myopic progression in children," Clin Exp Optom., 89:315-321 (2006).
Aleman, Andrea C., et al.,, "Reading and Myopia: Contrast Polarity Matters," Scientific Reports, 8 pages (2018).
Arden, G.B., et al., "Does dark adaptation exacerbate diabetic retinopathy? Evidence and a linking hypothesis," Vision Research 38:1723-1729 (1998).
Arden, GB, et al., "Regression of early diabetic macular edema is associated with prevention of dark adaptation", in Eye, (2011). 25, pp. 1546-1554.
Benavente-Perez, A., et al., "Axial Eye Growth and Refractive Error Development Can BE Modified by Exposing the Peripheral Retina to Relative Myopic or Hyperopic Defocus," Invest Ophthalmol Vis Sci., 55:6765-6773 (2014).
Bonar, Jr, et al, "High brightness low power consumption microLED arrays", in SPIE DigitalLibrary.org/conference-proceedings-of-spie, SPIE Opto, 2016, San Francisco, California, United States, Abstract Only.
Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).
Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).
Chakraborty, R., et al., "Monocular Myopic Defocus and Daily Changes in Axial Length and Choroidal Thickness of human Eyes," Exp Eye Res, 103:47-54 (2012).
Cooper, J., et al., "Current status of the development and treatment of myopia", Optometry, 83:179-199 (2012).
Cooper, J., et al., "A Review of Current Concepts of the Etiology and Treatment of Myopia," Eye & Contact Lens, 44(4):231-247 (Jul. 2018).
Demory, B., et al., "Integrated parabolic microlenses on micro LED color pixels", in Nanotechnology, (2018); 29, 16, pp. 1018, Abstract Only.
Dolgin, Elie, "The Myopia Boom," Nature 519:276-278 (2015).
Edrington, Timothy B., "A literature review: The impact of rotational stabilization methods on toric soft contact lens performance," Contact Lens & Anterior Eye, 34:104-110 (2011).
Flitcroft, D.I., "The complex interactions of retinal, optical and environmental factors in myopia aetiology," 31(6):622-660 (2012).
Garner, L.F., et al., "Crystalline Lens Power in Myopia," Optometry and Vision Science, 69:863-865 (1992).
Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).
Gwiazda, Jane, et al, "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).
Haglund, Erik, et al., "Multi-wavelength VCSEL arrays using high-contrast gratings," Proc. of SPIE vol. 10113, 7 pages (2017).
Hammond, D.S., et al, "Dynamics of active emmetropisation in young chicks—influence of sign and magnitude of imposed defocus" Ophthalmic Physiol Opt. 33:215-222 (2013).
Henry W., "MicroLED Sources enable diverse ultra-low power applications", in Photonic Spectra, 2013.
International Application No. PCT/US2021/036100, filedJun. 7, 2021 (86 pages).
International Patent Application No. PCT/US2021/032162, filed May 13, 2021 (58 pages).
International Patent Application No. PCT/US2021/036102, filed Jun. 7, 2021 (67 pages).
International Patent Application No. PCT/US2021/070166, filed Feb. 19, 2021 (79 pages).
International Search Report and Written Opinion for International Application No. PCT/US2019/030682, 8 pages (dated Jul. 17, 2019).
International Search Report and Written Opinion for International Application No. PCT/US2019/040580, 13 pages (dated Sep. 26, 2019).
International Search Report and Written Opinion for International Application No. PCT/US2020/044571, 17 pages (dated Nov. 19, 2020).
International Search Report and Written Opinion for PCT/US2019/043692, 14 pages (dated Dec. 3, 2019).
International Search Report and Written Opinion for PCT/US2020/070542, 11 pages (dated Dec. 21, 2020).
Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).
Jones, D., "Measure Axial Length to Guide Myopia Management," Review of Myopia Management, 5 pages (Apr. 9, 2020).
Kur, Joanna, et al., "Light adaptation does not prevent early retinal abnormalities in diabetic rats," Scientific Reports, 8 pages (Feb. 8, 2016).
Lagreze, Wolf A., et al., "Preventing Myopia," retrieved from https://www.ncbi.nlm.nih.gov/pmc/articles/PMC5615392/, Disch Arztebl Int., 114(35-36):575-580 (Sep. 2017).
Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).

(56) References Cited

OTHER PUBLICATIONS

Leo, Seo-Wei, et al., "An evidence-based update on myopia and interventions to retard its progression," J AAPOS, 15(2):181-189 (Apr. 2011).
Lingley, A.R., et al, : A single pixel wireless contact lens display, in J Micromech. Microeng., 2011; 21, 125014; doi:10.1088/0960-1317/21/2/125014, Abstract Only.
Martin, J.A., et al., "Predicting and Assessing Visual Performance with Multizone Bifocal Contact Lenses," Optom Vis Sci, 80(12):812-819 (2003).
Matkovic, K., et al., "Global Contrast Factor—a New Approach to Image Contrast," Computational Aesthetics in Graphics, Visualization and Imaging, 9 pages (2005).
McKeague C, et al. "Low-level night-time light therapy for age-related macular degeneration (ALight): study protocol for a randomized controlled trial", in Trials 2014, 15:246, http://www.trialsjournal.com/content/15/1/246.
Moreno, I, "Creating a desired lighting pattern with an LED array" in Aug. 2008, Proceedings of SPIE—The International Society for Optical Engineering 7058, DOI: 10.1117/12.795673.
Moreno, I., "Modeling the radiation pattern of LEDS", in Optics Express, 2008; 16, 3 pp. 1808.
Nickla, Debora L., et al., "Brief hyperopic defocus or form deprivation have varying effects on eye growth and ocular rhythms depending on the time-of-day of exposure," Exp Eye Res. 161:132-142 (Aug. 2017).
Ramsey, DJ, and Arden, GB, "Hypoxia and dark adaptation in diabetic retinopathy: Interactions, consequences and therapy", in Microvascular Complications-Retinopathy (JK Sun, ed.), Cur Dab Rep (2015) 15: 118, DOI 10.1007/s11892-015-0686-2, Abstract Only.
Read, Scott A., et al., "Choroidal changes in human myopia: insights from optical coherence tomography imaging," Clin Exp Optom, 16 pages (2018).
Read, Scott A., et al., "Human Optical Axial Length and Defocus," IOVS, 51(12):6262-6269 (2010).
Shivaprasad, S, et al, "Clinical efficacy and safety of a light mask for prevention of dark adaptation in treating and preventing progression of early diabetic macular oedema at 24 months (Cleopatra): a multicentre, phase 3, randomised controlled trial," in www.thelancet.com/diabetes-endocrinology vol. 6, pp. 382-391 ( May 2018).
Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).
International Search Report and Written Opinion for PCT/US2021/036097, 16 pages (dated Oct. 25, 2021).
Cook, Colin A., et al., "Photherapeutic Contact Lens for Diabetic Retinopahty," 2018 IEEE Micro Electro Mechanical Systems, pp. 62-65, XP033335512, (Jan. 21, 2018).

\* cited by examiner

LENS WITH ASYMMETRIC PROJECTION TO TREAT ASTIGMATISM

RELATED APPLICATIONS

This application is a continuation of International Application No. PCT/US2021/036097, filed Jun. 7, 2021, published as WO 2021/252318 A1 on Dec. 16, 2021, which claims the benefit under 35 U.S.C. § 119(e) of U.S. Provisional Patent Application No. 63/036,170, filed Jun. 8, 2020, and titled "LENS WITH ASYMMETRIC PROJECTION TO TREAT ASTIGMATISM," which are incorporated, in their entirety, by this reference.

The subject matter of the present application is related to International Patent Application No. PCT/US2019/043692, filed on Jul. 26, 2019, entitled "ELECTRONIC CONTACT LENS TO DECREASE MYOPIA PROGRESSION," published as WO 2020/028177 A1, and to U.S. Application No. 62/925,948, filed Oct. 25, 2019, entitled "DEVICE FOR PROJECTING IMAGES ON THE RETINA," the entire disclosures of which are incorporated herein by reference.

BACKGROUND

The eye refracts light to focus images onto the retina of the eye to provide vision. In some instances, however, the refraction of light may be less than ideal, which can lead to refractive error of the eye. The refractive error of the eye can be related to length of the eye and curvature of the cornea. For example, eyes with a longer axial length tend to be myopic, e.g. near sighted, and eyes with a shorter axial length tend to be hyperopic, e.g. far sighted. Eyes with irregularly shaped corneas tend to have astigmatism.

Astigmatism is generally related to an imperfection in the curvature of the eye's cornea or lens. In eyes without astigmatism, the cornea and lens are often curved substantially equally in all directions. In eyes with astigmatism, however, the cornea is often curved differently along different meridians of the cornea. An appropriately curved lens and cornea helps to focus light rays sharply onto the retina at the back of the eye.

When a cornea has an irregular shape, such that it is not curved equally in all directions, e.g. a toric shape, a patient may have corneal astigmatism. Astigmatism can cause a patient's vision to be blurry or distorted for both near and far objects.

Work in relation to the present disclosure suggests that the retina of many species, including human beings, responds to defocused images and grows in order to decrease the blur caused by the defocus. The mechanism of the generation of the growth signal is still under study, but an observable phenomena of the response of retinal tissue to the growth signal is the change in thickness of the choroid. A defocused image can cause the choroidal thickness to change, which may be related to changes to the axial length of the eye and the location of the retina with respect to the cornea and lens.

Astigmatism, myopia, and hyperopia are refractive errors of the eye that can be corrected with refractive lenses and surgery. However, at least some of these approaches can be less than ideal in at least some respects. For example, some patients may be contact lens or spectacle intolerant and refractive surgery can present risks. Uncorrected astigmatism can effect a person's ability to achieve and fully participate in school, sports, and other activities. Although spectacle lenses, contact lenses, and refractive surgery can be used to treat refractive errors of the eye such as astigmatism, such devices must be worn in order to correct the errors, and surgery comes with risks, such as infection and degraded vision. These prior approaches typically do not address the length of the globe, which can be related to retinal disease, such as retinal detachment, as the patient grows older.

While the defocus of images can play a role in choroidal thickness and changes in the axial length of the eye, the prior methods and apparatus are less than ideally suited to address astigmatism. For example, pharmaceutical treatments have been proposed to treat myopia associated with axial length growth, these treatments can have less than ideal results in at least some instances. Although light has been proposed as a stimulus to decrease changes in refractive error, the prior devices may be less than ideally suited to treat astigmatism with changes in retinal thickness in at least some instances.

Therefore, a new approach is needed to treat astigmatic refractive error of the eye.

SUMMARY

The presently disclosed methods and apparatus are capable of treating astigmatism with retinal stimulation. In some embodiments, a stimulus is configured to treat astigmatism with changes in retinal thickness, independently of, or in combination with, treatment for myopia. In some embodiments, a stimulus pattern is arranged with respect to an astigmatic axis of the eye to decrease ocular growth in relation to the astigmatic axis. In some embodiments, an apparatus is configured to direct light to regions of a retina outside the macula in relation to the astigmatic axis of the eye. In some embodiments, the stimulus intensity is modulated to provide the effect. While the stimulus can be provided in many ways, in some embodiments, a lens, such as a contact lens or spectacle lens is configured with a plurality of light sources, such as projection units having a light source and focusing optics that work together to project anteriorly or posteriorly defocused images onto the retina at locations eccentric to the fovea. In some embodiments, the stimulus promotes choroidal growth, which, in children and young adults, can slow the growth of the sclera near the stimulated locations. In some embodiments, the differential growth rates cause the eye to grow in such a way that ocular growth decreases the astigmatism of the patient.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus can be configured in many ways to provide retinal stimulation as described herein. The presently disclosed methods and apparatus are well suited for combination with many prior devices such as, one or more of an ophthalmic device, a TV screen, a computer screen, a handheld mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. Although specific reference is made to spectacles and contact lenses, the presently disclosed methods and apparatus are well suited for use with any of the aforementioned devices, and a person of ordinary skill in the art will readily appreciate how one or more of the presently disclosed components can be interchanged among devices, based on the teachings provided herein.

Work in relation to the present disclosure suggests that changes to choroidal thickness in response to stimulation can be localized to regions near the stimulated regions, which can provide a somewhat localized response in accordance with some embodiments. In some embodiments, the changes to one or more of the choroid or sclera comprise a differential change, in which the changes to the one or more of the choroid or sclera are greater near the regions of stimulation than at corresponding regions remote from the stimulation (e.g. corresponding locations at an axis 90 degrees from the region of stimulation).

Figure 1:
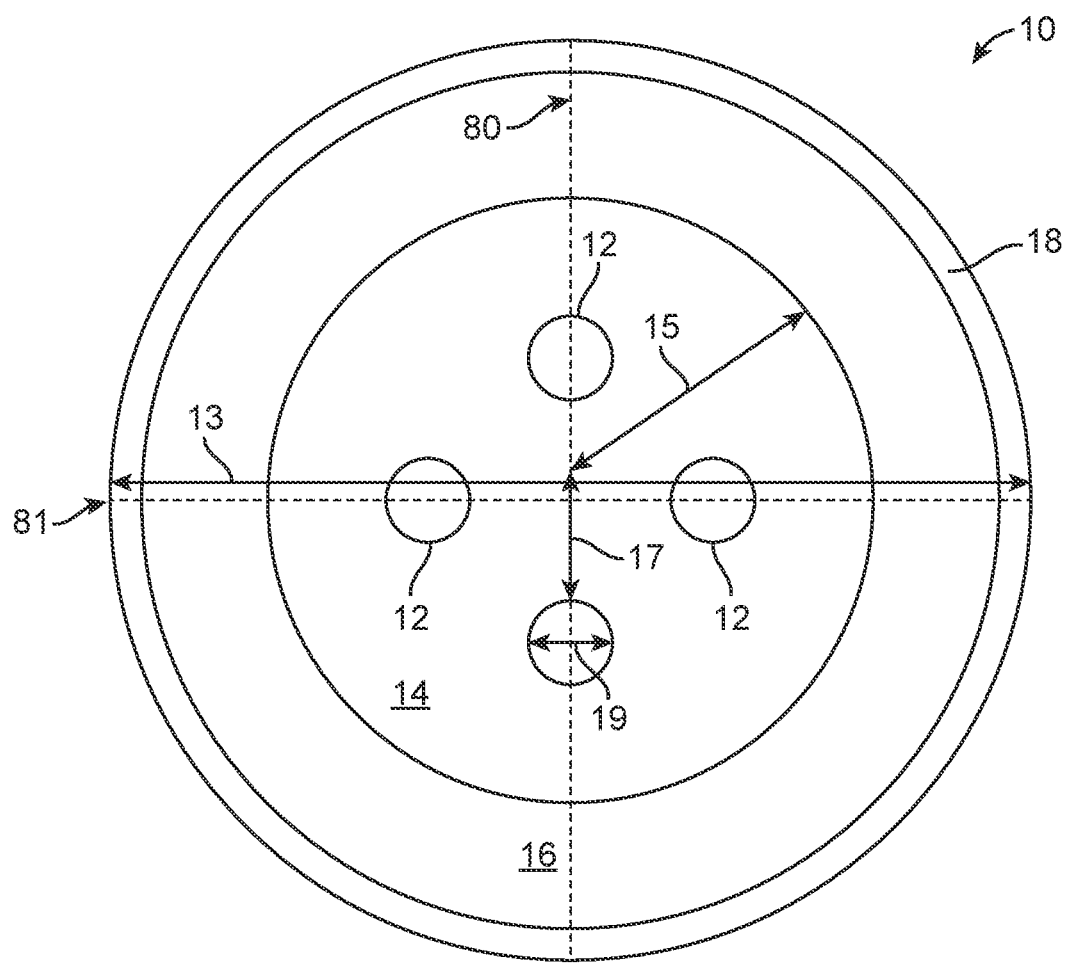
FIG. 1 shows a soft contact lens, in accordance with some embodiments.
Figure 2:
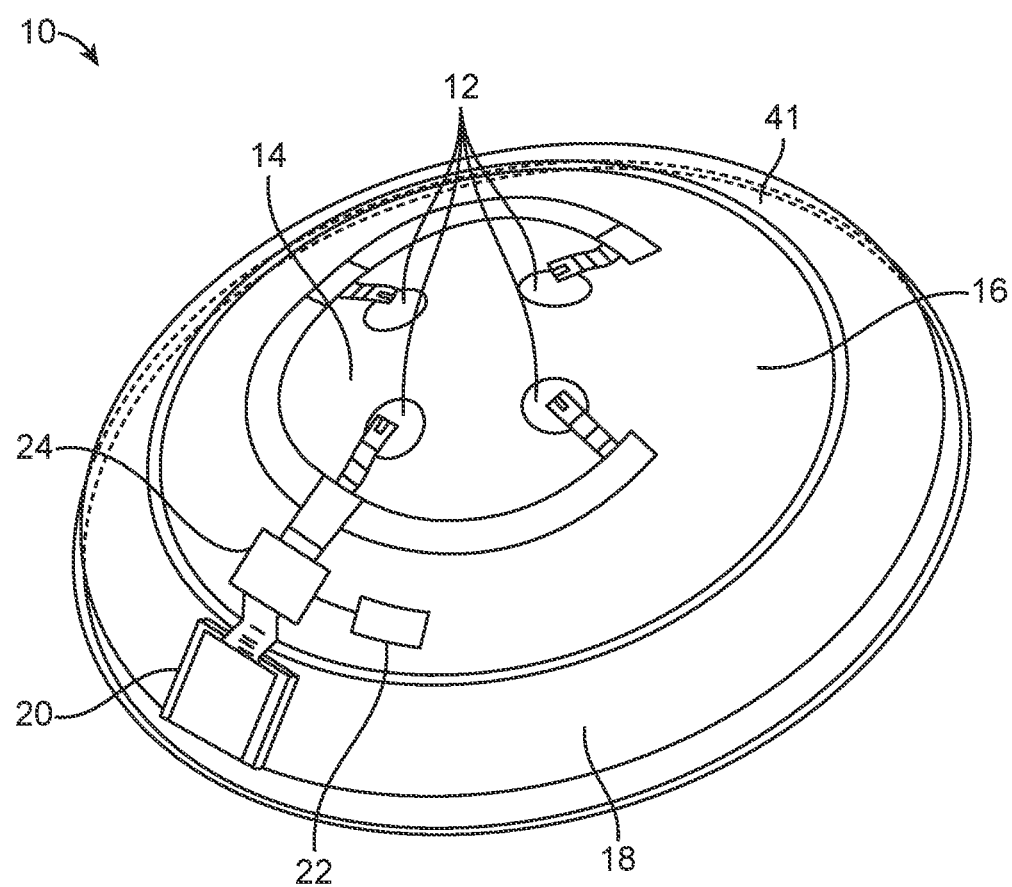
FIG. 2 shows soft contact lens with embedded light sources, optics and electronics for projecting images with defocus on the periphery of the retina of a wearer, in accordance with some embodiments.

FIGS. 1 and 2 depict a lens such as a contact lens 10 configured to project a defocused image on the retina away from the central field that includes the macula in order to stimulate a change in choroidal thickness. Although reference is made to a contact lens, the lens 10 may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

In some embodiments, the contact lens 10 comprises a first astigmatic axis 80 and a second astigmatic axis 81. The plurality of light sources, such as projection units 12, is arranged with respect to the astigmatic axes to provide different amounts of stimulation to different regions of the peripheral retina. In some embodiments, the light sources such as projection units 12 are located along the astigmatic axis, although the light sources may be located at other locations. The light sources can be configured to provide different amounts of stimulation to the peripheral retina in accordance with the refractive error of the eye. In some embodiments, the light sources are configured to provide different amounts of illumination along different axes in order to promote different changes in choroidal and scleral tissue corresponding to different changes in axial length as described herein. The contact lens may comprise a rotationally stabilized contact lens, and the light sources can be located on the contact lens so as to correspond to the astigmatic axes of the eye when the lens is stabilized on the eye, for example. The contact lens may comprise an optical zone configured to correct astigmatic refractive errors in accordance with the first axis 80 and the second axis 81.

This contact lens 10 comprises a base or carrier contact lens comprising embedded electronics and optics. The base soft contact lens 10 is made of a biocompatible material such as a hydrogel or a silicone hydrogel polymer designed to be comfortable for sustained wear. The contact lens comprises a maximum overall distance across, e.g. a diameter 13. The biocompatible material can encapsulate the components of the soft contact lens 10. In some embodiments, the contact lens 10 has a central optical zone 14 designed to cover the pupil of a wearers under many illumination conditions. In some embodiments, the optical zone comprises a circular zone defined with a radius 15. In some embodiments, a plurality of projection units 12 is located a distance 17 from a center of the optical zone. Each of the plurality of projection units 12 comprises a distance across 19. In some embodiments, the distances between the projection units are sized to place the projection units outside the optical zone to stimulate a peripheral region of the retina, although the projection units can also be placed inside the optical zone to stimulate the peripheral retina as described herein.

The optical zone 14 can be appropriately sized for the pupil of the eye and the illumination conditions during treatment. In some embodiments, the optical zone comprises a diameter of 6 mm, for example when the contact lens is configured for use during the day. The optical zone 14 may have a of diameter within a range from 6 mm to 9 mm, for example within a range from 7.0 mm to 8.0 mm. The central optical zone 14 is designed to provide emmetropic correction or other suitable correction to the wearer, and may be provided with both spherical and astigmatic correction. The central optical zone 14 is circumscribed by an outer annular zone, such as a peripheral zone 16 of width in a range 2.5 mm to 3.0 mm. The peripheral zone 16, sometimes referred to as the blend zone is primarily designed to provide a good fit to the cornea, including good centration and minimum decentration. The outer annular zone is surrounded by an outermost edge zone 18 of width in the range from 0.5 mm to 1.0 mm. The optical zone 14 is configured to provide refractive correction and can be spherical, toric or multifocal in design, for example with a visual acuity of 20/20 or better. The outer annular zone peripheral to the optical zone 14 is configured to fit the corneal curvature and may comprise rotational stabilization zones for translational and rotational stability, while allowing movement of the contact lens 10 on the eye following blinks. The edge zone 18 may comprise a thickness within a range from 0.05 mm to 0.15 mm and may end in a wedge shape. The overall diameter 13 of the soft contact lens 10 can be within a range from 12.5 mm to 15.0 mm, for example within a range from 13.5 mm to 14.8 mm.

The contact lens 10 includes a plurality of embedded projection units 12. Each of the plurality of projection units 12 comprises a light source and one or more optics to focus light in front of the retina as described herein. Each of the optics may comprise one or more of a mirror, a plurality of mirrors, a lens, a plurality of lenses, a diffractive optic, a Fresnel lens, a light pipe or a wave guide. The contact lens 10 may comprise a battery 20 and a sensor 22. The contact lens 10 may comprise a flex printed circuit board (PCB) 24, and a processor can be mounted on the flex PCB 24. The processor can be mounted on the PCB 24 and coupled to the sensor 22 and the plurality of light sources 30. The soft contact lens 10 may also comprise wireless communication circuitry and one or more antennae 41 for electronic communication and for inductively charging the battery 20 of the contact lens 10. Although reference is made to a battery 20, the contact lens 10 may comprise any suitable energy storage device.

The projection units 12 can be configured to provide defocused images to the peripheral portion of the retina as described herein and may include light sources and projection optics. In some embodiments, one or more projection optics are configured with the light sources to project a defocused image from the light sources onto the peripheral retina away from the central visual field that includes the macula in order to stimulate a change in choroidal thickness, such as an increase or decrease in cordial thickness. The one or more projection units 12 can be configured to stimulate the retina without degrading central vision and corresponding images formed on one or more of the foveal or macular regions of the retina. In some embodiments, the one or more projection optics do not decrease the image forming characteristics of the vision correction optics prescribed to correct refractive errors of the wearers. This configuration can allow the wearer to have good visual acuity while receiving therapy from the defocused images as described herein.

In some embodiments, the light from light sources of the projection units 12 are columnated and focused by one or more projection optics, as described herein. The function of the light sources and the projection optics is to substantially collimate the light emitted by the light sources and focus it at a focus that is designed to be in the front of or behind the retina to provide appropriate defocus to stimulate a change in choroidal thickness. For myopic defocus, the focused images may appear approximately 1.5 mm to 2.5 mm in front of the peripheral retina and myopic by about 2.0 D to 5.0 D, for example 2.0 D to 4.0 D, or preferably 2.5 D to 3.5 D, for example. For hyperopic defocus, he focused images may appear approximately 1.5 mm to 2.5 mm behind of the peripheral retina, in order to be hyperopic by about −2.0 D to −5.0 D, for example −2.0 D to −4.0 D, or preferably −2.5 D to −3.5 D, for example.

In accordance with some embodiments, a soft contact lens 10 comprises projection units which include projection optics and micro-displays as the light source. The micro-displays may comprise an OLED (organic light emitting diode) or an array of micro-LEDs. Light emitted by these displays may be Lambertian. In some embodiments, the micro-display is optically coupled to a micro-optical array that substantially collimates and focuses the light emanating from the micro-display. The micro-display may comprise one or more miniaturized pixels. In some embodiments, the micro-display forms an extended array of pixels, characterized by a pixel size and a pixel pitch, in which the pixel size and the pixel pitch together correspond to a fill factor of the micro-display. As described herein, each of the pixels may have a size within a range from about 2 microns to about 100 microns, and the pixel pitch may range from 10 microns to 1.0 mm, for example. The corresponding fill factor can range from 0.1% to 10%. In some embodiments, the pixel array is optically coupled with a micro-optic array in order to substantially collimate and focus light from the pixels.

The images created by these displays is defocused and may be placed symmetrically in four quadrants of the field of view or of the eye (e.g. nasal-inferior, nasal-superior, temporal-inferior and temporal-superior). The micro displays can be located away from the optical center of the lens by a distance within a range from 1.5 mm to 4.0 mm, preferably 2.5 mm to 3.5 mm. The central optic of the contact lens can be selected to bring the wearer to emmetropia, and may have a diameter within a range 3.0 to 5.0 mm. Each micro-display may be circular, rectangular or arcuate in shape and have an area within a range from 0.01 mm2 to 8.0 mm2, for example within a range from 0.04 mm2 to 8.0 mm2, for example within a range from 1 mm2 to 8 mm2, or preferably within a range from 1.0 mm2 to 4.0 mm2, in some embodiments.

The micro-display can be coupled to and supported with the body of the correction optic such as a contact lens, or a spectacle lens, an augmented reality ("AR") headset, or a virtual reality ("VR") headset for example. In some embodiments, the micro-displays are coupled to and supported with one or more of an intraocular lens, a corneal prosthesis, a corneal onlay, or a corneal inlay. The optical configurations described herein with reference to a contact lens can be similarly used with one or more of an intraocular lens, a corneal prosthesis, a corneal onlay, or a corneal inlay, for example.

In some embodiments, the micro-displays and the micro-optic arrays are mounted immediately adjacent to each other on the same correction optic, separated by a fixed distance in order to project a bundle of rays to the pupil of the eye, at an orientation that it forms a defocused image at a desired location on the retina as described herein. In some embodiments, the one or more projection optics are mounted on or in the one or more correction optics, such that rays from the projection optics are refracted through the correction optics.

The correction optics refract the rays from the projection optics to be convergent or divergent as helpful for clear vision, so that the micro-optical array can provide the desired magnitude of additional power that may be plus or minus, depending on the magnitude and sign of the defocus desired. The micro-display may be monochromatic or polychromatic, for example.

In some embodiments, the projected defocused image can be provided by a micro-display comprising a screen comprising one or more of an LCD screen, a screen driven by OLEDS (organic light emitting diodes), TOLEDS, AMOLEDS, PMOLEDS, or QLEDS. The screen may appear to the subject at a far distance of east least 6 meters or more, for example.

Figure 3:
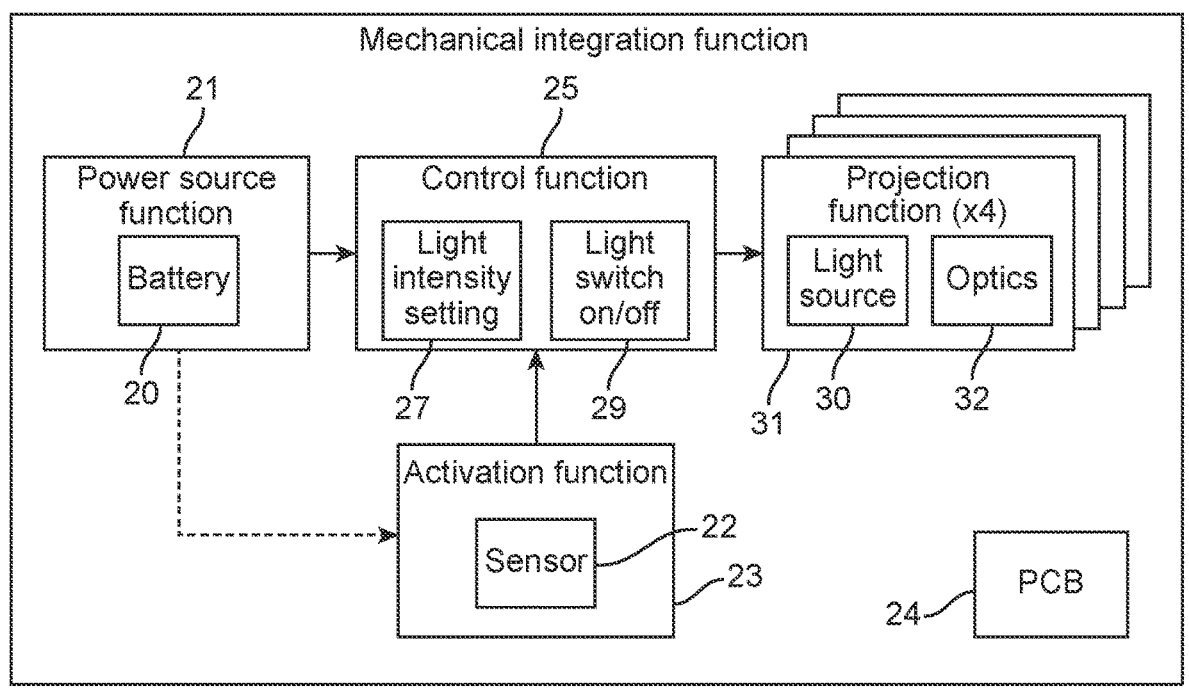
FIG. 3 shows mechanical integration of the function of the components of a lens as in FIG. 2.

FIG. 3 shows mechanical integration of the function of the components of a retinal stimulation device, such as a contact lens 10 as in FIG. 2. Although reference is made to mechanical integration with a contact lens, similar integration can be performed with any vision device as described herein. These components can be supported with the PCB 24. For example, the power source such as a battery 20 can be mounted on the PCB 24 and coupled to other components to provide a power source function 21. The sensor 22 can be configured to provide an activation function 23. The sensor 22 can be coupled to a processor mounted on the PCB 24 to provide a control function 25 of the contact lens 10. The control function 25 may comprise a light intensity setting 27 and a light switch 29. The processor can be configured to detect signal from the sensor 22 corresponding to an increase in intensity, a decrease in intensity, or an on/off signal from the sensor 22, for example with a coded sequence of signals from the sensor 22. The processor is coupled to the light projection units 12 which can comprise a light source 30 and optics 32 to provide the projection function 31. For example, the processor can be coupled to the plurality of light sources 30 to control each of the light sources 30 in response to user input to the sensor 22.

The retinal stimulation device may comprise global positioning system (GPS) circuitry for determining the location of the wearer, and an accelerometer to measure body movement such as head movement. The retinal stimulation device may comprise a processor coupled to one or more of the GPS or the accelerometer to receive and store measured data. The retinal stimulation device may comprise communication circuitry such as wireless communication circuitry, e.g. Bluetooth or WiFi, or wired communication circuitry, e.g. a USB, in order to transmit data from the device to a remote server, such as a cloud-based data storage system. This transmission of data to the remote server can allow the treatment and compliance of the wearer to be monitored remotely. In some embodiments, the processor comprises a graphics processing unit (GPU). The GPU can be used to efficiently and rapidly process content from the web in order to utilize this content in forming the stimulus as described herein.

The methods and apparatus for retinal stimulation as described herein can be configured in many ways and may comprise one or more attributes to encourage a user to receive therapy. For example, the retinal stimulation as described herein can be combined with a display of a game to encourage a user to wear the treatment device. In some embodiments, the retinal stimulation can be combined with another stimulus, such as an emoji, e.g. a smiley face, to encourage a user to wear the device for treatment. The components of the system may communicate with or receive information from a game or other stimulus to facilitate the retinal stimulation with the game or stimulus.

Figure 4A:
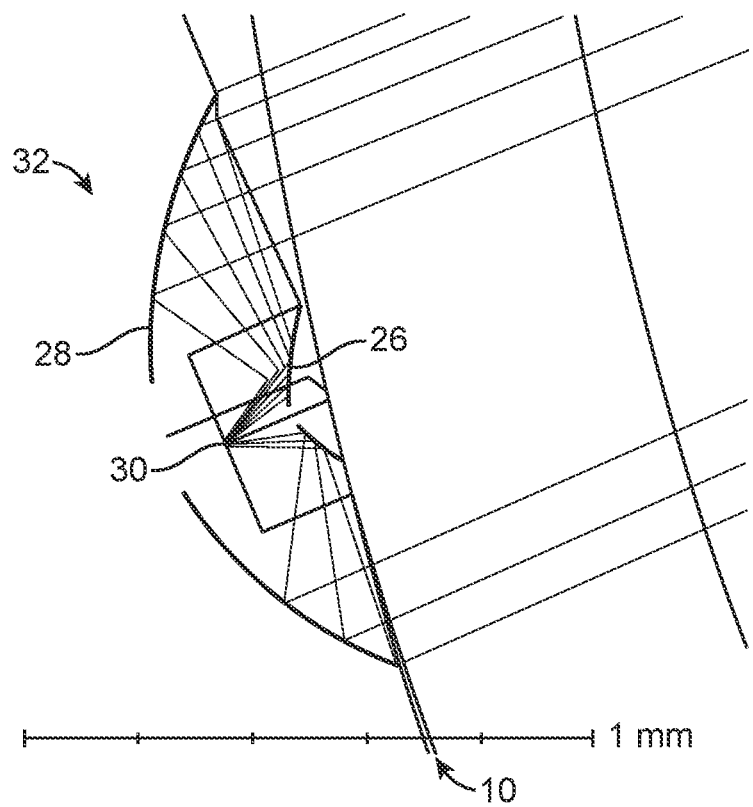
FIG. 4A shows an optical configuration in which the optical path length is increased by folding the optical path with two mirrors, in accordance with some embodiments.
Figure 4B:
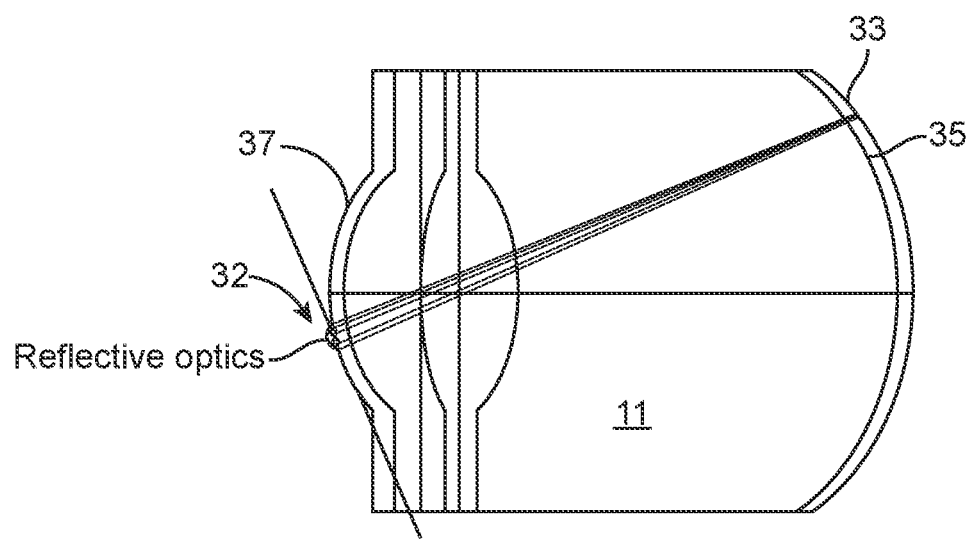
FIG. 4B shows a ray tracing simulation of the optical configuration shown in FIG. 4A, in accordance with some embodiments.

Referring to FIG. 4A, In some embodiments, the optic configuration 32 comprises a plurality of mirrors configured to collect light emitted by the micro-displays 12, then direct the light beam to the pupil of the eye 11, in order to form an eccentric retinal image, as shown in FIG. 4B. The mirrors may substantially collimate the light beam, or direct the light beam toward the retina 33 with a suitable vergence so as to focus the light beam onto the retina 33.

Although the optic configurations shown in FIGS. 4A and 4B refer to a lens, such as a contact lens, a similar optical configuration can be used with a lens of one or more of a projector, an ophthalmic equipment, a TV screen, a computer screen, a handheld device such as a smart phone, a wearable device such as a spectacle lens, a near eye display, a head-mounted display, an AR display, a VR display, a goggle, a contact lens, a corneal onlay, a corneal inlay, a corneal prosthesis, or an intraocular lens. Also, although reference is made to a myopic defocus, the defocus may comprise a hyperopic defocus, or an image focused onto the retina, or other defocus for the correction of refractive error as described herein, for example.

The mirror assembly shown in FIG. 4A can be configured to achieve a depth of focus that is less than 1 D, enabling the applied defocus of 2.0-4.0 D to be clearly perceived by the peripheral retina 33 at the specified eccentricity (e.g. within a range from 20 degrees to 30 degrees).

Figure 5A:
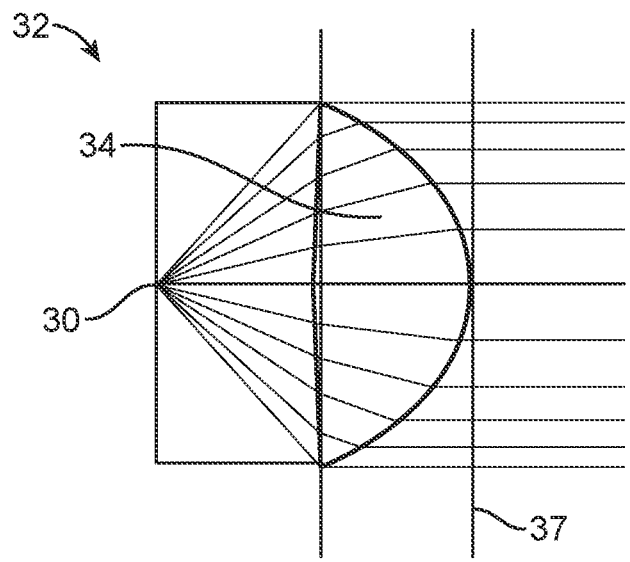
FIG. 5A shows an optical configuration comprising a lens to focus light onto the retina, in accordance with some embodiments
Figure 5B:
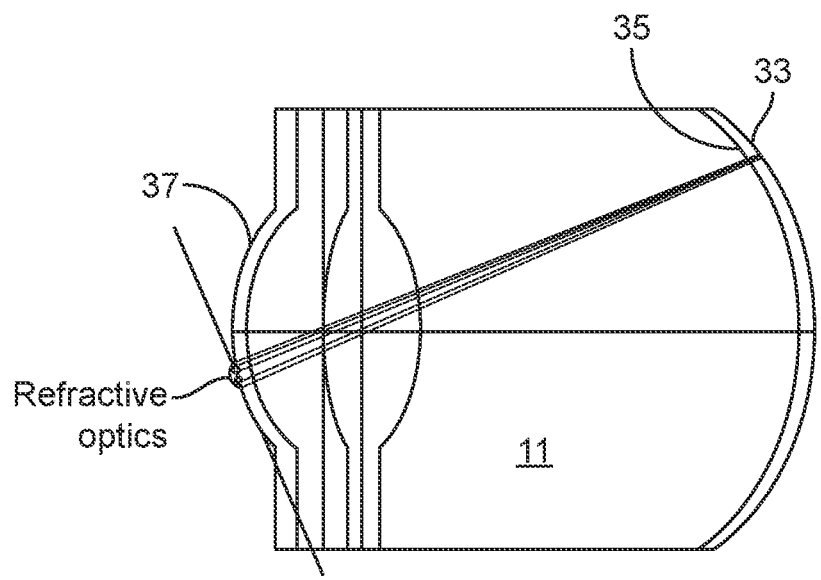
FIG. 5B shows a ray tracing simulation of the optical configuration shown in FIG. 5A, in accordance with some embodiments.

As shown in FIGS. 5A and 5B, another embodiment comprises optics 32 comprising a converging or collimating lens in optical coupling with light source 30. In this configuration a lens 34, which may comprise a single lens, is used to substantially collimate the light output from the stimulation source and direct it to the cornea 37 through the lens such as contact lens 10. Although reference is made to a contact lens, the lens may comprise a lens of one or more of a projector, an ophthalmic equipment, a TV screen, a computer screen, a handheld device such as a smart phone, a wearable device such as a spectacle lens, a near eye display, a head-mounted display, a VR display, and AR display a goggle, a contact lens, a corneal onlay, a corneal inlay, a corneal prosthesis, or an intraocular lens.

The effectiveness of the collimating lens 34 depends on its refractive index and should be sufficiently high in order to create a substantial difference in refractive indices between the lens material and the material of the contact lens 10 that functions as the substrate. In this example, the refractive index of the embedded lens 34 has been assumed to be 2.02 (e.g., refractive index of a lanthanum fluorosilicate glass LaSF5), although other materials may be used.

Figure 6A:
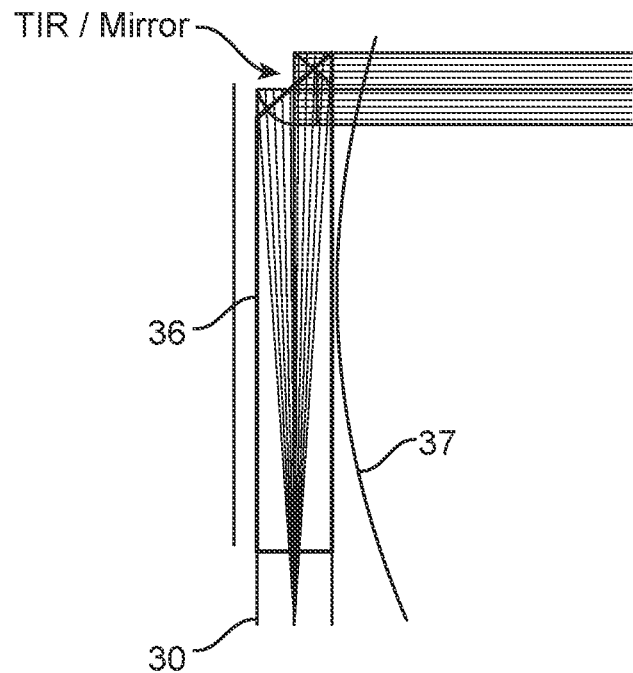
FIG. 6A shows a light-pipe, in accordance with some embodiments.
Figure 6B:
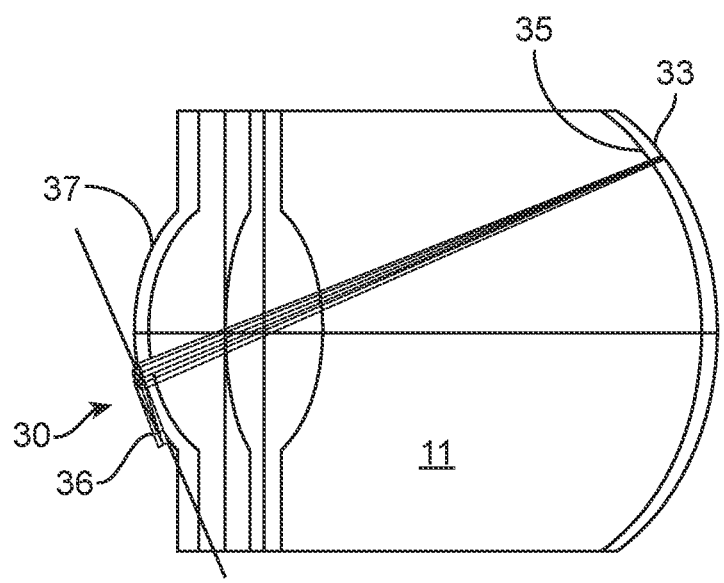
FIG. 6B shows a ray tracing simulation of the optical configuration shown in FIG. 6A, in accordance with some embodiments.

Another embodiment comprises a light-pipe 36, as shown in FIGS. 6A and 6B. The light-pipe 36 can provide an increased optical path length to decrease image magnification and retinal image size in order to provide higher spatial frequencies to the image projected on the retina, in accordance with some embodiments.

Although reference is made to a light pipe 36 on a cornea 37 as would occur with a contact lens, the lens combined with the light pipe 36 may comprise a lens of one or more of a projector, an ophthalmic equipment, a TV screen, a computer screen, a handheld device such as a smart phone, a wearable device such as a spectacle lens, a near eye display, a head-mounted display, a VR display, an AR display, a goggle, a contact lens, a corneal onlay, a corneal inlay, a corneal prosthesis, or an intraocular lens.

Numerous other optical configurations may be used, including the use of a micro-lens array with a point source, use of diffractive optics in order to use a thinner lens, generation of multiple retinal images using a single point source and an optical processing unit. In all case, the three characteristics listed above may be used as metrics in order to evaluate the suitability of a particular design.

Figure 7A:
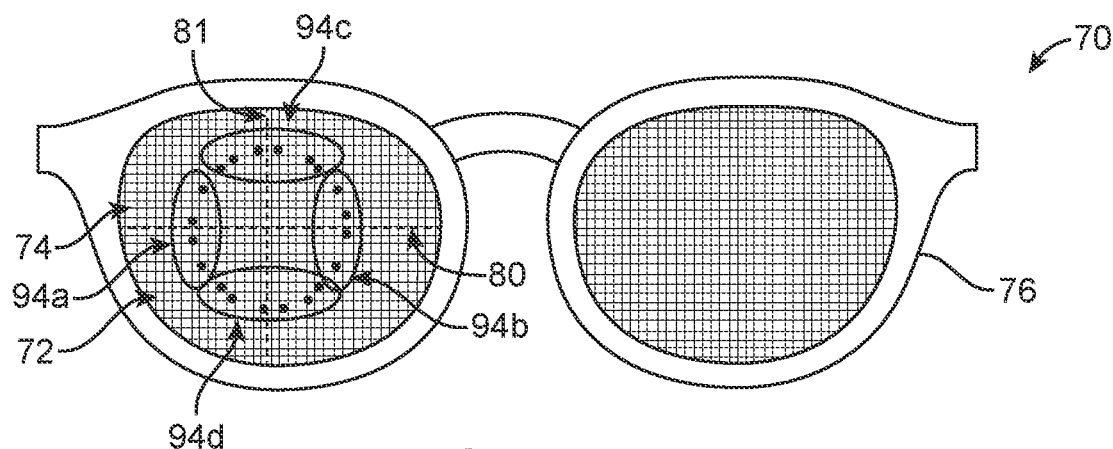
FIG. 7A shows a spectacle lens based retinal stimulation device comprising a display and a housing to contain the electronics for operating the near eye display, in accordance with some embodiments.
Figure 7B:
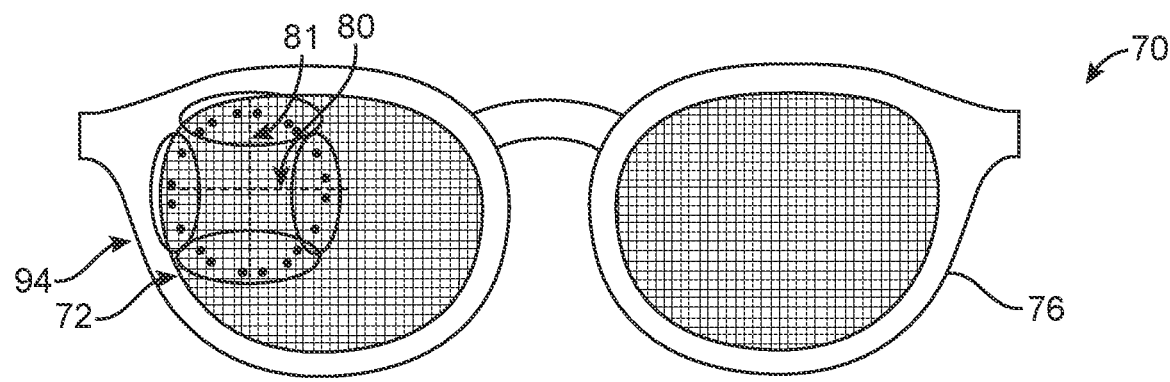
FIG. 7B shows a spectacle lens based retinal stimulation device as in FIG. 10A, in which the eye has moved and different display elements have been activated in response to the eye movement, in accordance with some embodiments.

FIGS. 7A and 7B depict spectacles 70 for the treatment of refractive error of the eye, such as spherical and astigmatic refractive error. Although reference is made to spectacles, the light sources can be provided on any vision device described herein to treat astigmatism. In some embodiments, the spectacles comprise a first a first astigmatic axis 80 and a second astigmatic axis 81. A plurality of light sources is arranged to treat astigmatism in accordance with the astigmatic axes of the eye. The plurality of light sources may comprise any suitable light source as described herein, such as a micro display or projection units, for example. In some embodiments, the light sources are configured to provide different amounts of illumination along different axes in order to promote different changes in choroidal and scleral tissue corresponding to different changes in axial length as described herein. The lens may comprise an optical zone with optical properties, e.g. refractive properties, configured to correct astigmatic refractive errors in accordance with the first axis 80 and the second axis 81. This refractive treatment of astigmatism can be combined with retinal stimulation as described herein.

The spectacles 70 may comprise one or more components of commercially available augmented reality glasses. The spectacle 70 may comprise one or more displays 72 for retinal stimulation. The near eye displays 72 may be mounted to lenses 74. The lenses 74 may be spectacle lenses supported by eyeglass frame 76. The lens 74 may be a corrective or non-corrective lens. The lens 74 may be a plano lens, a spherical corrective lens, an astigmatic correction lens, or a prism correction lens. In some embodiments, the near eye display is located away from an optical zone to provide clear central vision. An optical axis may extend along a line of sight from an object of the patient's regard, though the lens 74 to a fovea of the eye. In some embodiments, the spectacle 70 comprises an eye tracker suitable for incorporation in accordance with the present disclosure. The near eye display 72 can be programmed to selectively activate pixels 94, in order to provide peripheral stimulation to the retina, as described herein. In some embodiments, a layer of a plastic substrate bearing micro-lenses is attached to the micro-display in order to generate the desired level of defocus and stimulation at the retina. The selectively activatable pixels may comprise a groups of pixels, which can be selectively activated together, e.g. a first group of pixels 94*a*, a second group of pixels 94B, a third group of pixels 94C, and a fourth group of pixels 94D. The groups of pixels can be arranged to provide an appropriate eccentricity with respect to a line of sight of the patient, so as to provide peripheral retinal stimulation as described herein.

In some embodiments a near eye display 72 comprises a combination of a micro-display and a micro-optic. In some embodiments, the micro-optic is configured to collect, substantially collimate and focus the light rays emanating from the micro-display. In some embodiments, the micro-optic is configured to form an image anterior to or posterior to the retina as described herein. In some embodiments, the distance of the near eye display from the entrance pupil of the eye is within a range from about 10 mm to about 30 mm, for example about 15 mm. The micro-display can be placed on a transparent substrate, such as the front or back surface of the lens 74 of the spectacles 70. When the micro-display is placed on the front surface of the lens 74, then the focus of the micro-displays may be affected by the cylindrical correction on the back surface of the lens 74.

In some embodiments, the focus of the pixels in a micro-display may vary based on their location on the lens 74 and the refractive correction provided by the lens in that area. In some embodiments, the focus of the pixels may be fixed. In some embodiments, the focus of the pixels may vary based on the sensed position of the cornea to account for the refraction of the cornea and the lens of the eye. In some embodiments, the pixels are defocused to create a defocused spot on the retina about 1 mm in diameter.

Light emitted by the pixels 94 in the micro-display of the near eye display can be one or more of substantially collimated or focused before being directed to the pupil of the eye. In some embodiments, a micro-lens array is aligned to the pixels of the near eye display, so that rays from the near eye display can enter the pupil and form an image anterior to or posterior to the retina. In some embodiments, the width of the near eye display corresponds to a patient's field of view. In some embodiments, the extent of the near eye display may be substantially similar to the extent of the lens 74 of the spectacles 70.

In some embodiments, the device provides unimpaired central vision so that the quality of life and quality of vision of the wearers are not adversely affected. In some embodiments, central vision comprises of a field of view of +/−12.5 degrees, covering the macula, while foveal vision used for fixation has a field of view of +/−2.0 degrees. In some embodiments, the defocused image is projected at an outer portion of the retina toward the periphery of the retina, for example within a range from 15 degrees to 40 degrees eccentric to the fovea and can be within a range from 20 degrees to 30 degrees. In some embodiments, the micro-display 72 does not obstruct the central vision field of view. In some embodiments, the pixels 94 do not obstruct the central vision field of view.

In some embodiments, the micro-displays and optics are configured to project light onto outer regions of the retina sufficiently far from the fovea, that the illumination remains substantially fixed even with eye movement. In some embodiments, the point of regard is monitored and the desired location of the pixels to be activated on the micro-display is determined, e.g. by a computations with a processor, such that an image is projected at the desired location on the retina, allowing persistent stimulation at the same retinal location. In some embodiments, the point of regard on the spectacle plane or the plane of the micro-display is calculated by monitoring the horizontal, the vertical and torsional displacement of the eye relative to the primary position.

The point of regard can be determined with a in many ways, for example with an eye position sensor such as a magnetic sensor or an optical sensor. In some embodiments, a search coil embedded in the eyeglass frame is used to track eye movements. The coil embedded in the eyeglass frame can be coupled to a magnetic structure placed on the eye, such as one or more of a coil on a contact lens, a coil implanted in the eye, a magnetic material on a contact lens, or a magnetic material implanted in the eye. In some embodiments, the sensor comprises an optical sensor, such as a position sensitive detector or an array sensor to measure a position of the eye optically. The optical sensor can be configured to measure a position of the eye in many ways, for example configured to measure a position of one or more of a corneal reflex from a light source, a pupil, a limbus or a sclera. The eyeglass frame may support an additional light source to illuminate the eye, for example to generate a corneal reflex. Data from the sensor can provide the location of the coaxially lighted corneal light ("CSCLR"), and hence the direction of the visual axis and the location of the fovea. In some embodiments, the processor, using the eye position sensor, may be configured to adjust the optics, such as the pixels in the micro display to reduce movement of the stimulated locations of the retina in response to eye movement. In some embodiments, target locations of the peripheral images are computed from the location of the fovea based on the information form the eye position sensor and a real time ray tracing calculation provides the locations of the pixels to be activated in the micro-display. The time to selectively switch to a second plurality of pixels in response to the eye movement can be less than 100 milliseconds, for example less than 20 milliseconds.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard. For example, FIG. 7A shows active pixels 94 when a patient is looking level and straight ahead, so-called primary gaze, while FIG. 7B shows active pixels 94 when a patient is looking up and to the left. In such a case, the shape of the array of pixels may be the same, but translated up and to the left, or the shape of the array may change. In some embodiments, the plurality of light sources, e.g. active pixels 94, are configured to change so as to maintain alignment of the first astigmatic axis 80 and the second astigmatic axis 81 with respect to the eye when these axes are translated, for example. This translation and alignment can be provided with processor instructions configured to selectively activate pixels in accordance with the eye movement and the first astigmatic axis 80 and the second astigmatic axis 81.

In some embodiments, the device is binocular and comprises a micro-display and optics for each eye of the wearer. The micro-display can be optically coupled with one or more micro-optical components, designed to substantially collimate the illumination generated by the pixels of the micro-display and rendered convergent, before entering the pupil.

In some embodiments, a display 72 is mounted on the outer side of a spectacle lens and aligned with the spectacle lens optic such that the near eye display can provide a field of view of +/−40 degrees or greater, so that the micro-display can continue to provide peripheral retinal stimulus for the normal range of eye movements, typically +/−15 degrees laterally and +10 to −20 degrees vertically, including downgaze when reading or viewing near objects. In some embodiments, light from the micro-display is transmitted through the spectacle lens optic and provided with the refractive correction of the wearer.

In some embodiments, the optical system is configured to form the images anterior to the retina and comprises one or more of a single micro-lens (lenslet), a plurality of micro-lenses (lenslet array), a compound lens, such as a Gabor lens, a micro-prism, or a micro-mirror, or a combination thereof. In some embodiments, light baffles and micro-mirrors are arranged to ensure that the amount of light not captured by the micro-optic is substantially decreased, e.g. minimized, in order to reduce stray light and light escaping from the front side of the display.

In some embodiments, a pixel fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns leads to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels 94 can be collected, collimated and focused to be directed to the pupil of the wearer at primary gaze. The density of these micro-optical elements can control the overall visibility of the near eye display. In some embodiments, the micro-optic has a low fill factor (preferably equal to or less than 0.1) so that the overall light transmission through the near eye display will be acceptable to wearers and allow the patient to view objects.

In some embodiments the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard.

In some embodiments, a plurality of pixels is activated to form the light source that is imaged by the micro-optics. The optical design of the micro-optics and its separation from the micro-display can be configured to provide the focal length of the image delivery system, the image magnification of the image projected on the retina and the blur caused by diffraction, as measured as the Airy disc diameter of the optical delivery system.

Work in relation to the present disclosure suggests that the retina perceives changes in image blur caused by higher order aberrations present in the defocused image (in addition to the spherical defocus), including longitudinal chromatic aberration (LCA), higher order spherical aberration, astigmatism, etc. that are sensitive to the sign of the defocus. Based on the teachings provided herein a person of ordinary skill in the art can conduct experiments to determine whether the retina can recognize a myopic blur from a hyperopic blur when the depth of focus of the device is greater than or nearly equal to the magnitude of defocus. The device as described herein can be appropriately configured to provide appropriate amounts of defocus at appropriate locations, for example.

The device can be configured to provide appropriate image magnification, diffraction that limits the image resolution and depth of focus in relation to the magnitude of myopic defocus being applied and the rate of change of image blur or image sharpness gradient as a function of the magnitude of defocus.

In some embodiments, the near eye display is configured to provide a clear, substantially undistorted field of view of the foveal and macular image for comfortable vision. In some embodiments, the field of view of the central image is at least +/−12 degrees and can be more in order to account for differences in interpupillary distance (IPD) of different wearers. Image quality and field of view of the real image can be provided with a substantially transparent near eye display transparent, and by reducing the fill factor of light emitting pixels in the micro-display. In some embodiments, a fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns will lead to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels can be collected, collimated and focused to be directed to the pupil of the wearer at primary gaze. The population density of these micro-optical elements can control the overall visibility of the near eye display. In some embodiments, the micro-optic has a low fill factor (preferably equal to or less than 0.1) so that the overall light transmission through the near eye display will be acceptable to wearers.

In some embodiments the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

Figure 8:
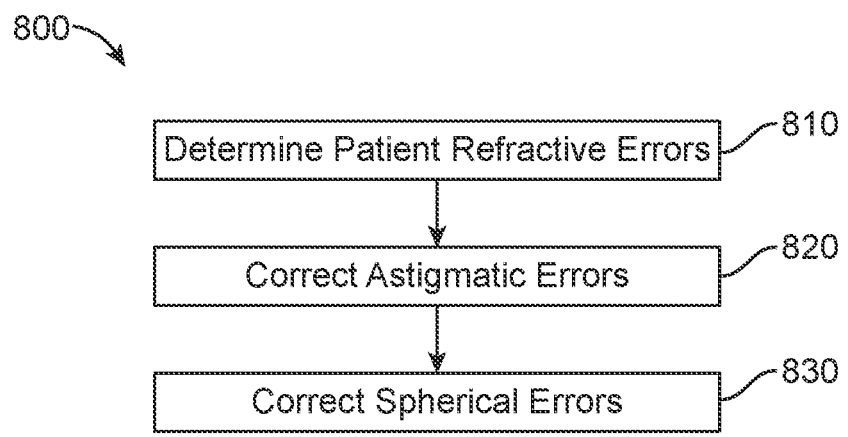
FIG. 8 shows a method of treating refractive errors of the eye, in accordance with some embodiments.

The systems and apparatus discussed above may be used in the treatment of astigmatism, independently of, or in combination with, treatment for myopia or hyperopia, for example. FIG. 8 shows a method 800 for treating refractive errors of patient's eye or eyes. At step 810, the refractive error of the patient's eye is determined.

The astigmatism of the eye can be determined in many ways. Suitable approaches for determining the astigmatism of the eye include one or more of manifest refraction with a phoropter, auto-refraction, retinoscopy, corneal topography, wavefront measurements, Scheimpflug imaging, optical coherence tomography, Hartmann Shack wavefront aberrometry, and other approaches to measuring astigmatism as is known to one of ordinary skill in the art.

If astigmatic error is found at step 810, then at step 820, the astigmatic error of the patient's eye is corrected. If spherical error is found at step 810, then at step 830, the spherical errors of the patient's eye is corrected. In some embodiments, the correction of the errors at step 820 and step 830 may occur in parallel or in series. For example, in some embodiments, correction of astigmatic error in step 820 may occur before the correction of spherical error in step 830. In some embodiments, the treatment may be reversed, wherein the correction of spherical errors in step 830 may occur before the correction of astigmatic errors in step 820. Still, in other embodiments, the treatment of spherical errors at step 830 and the treatment of astigmatic errors at step 820 may occur at the same time, for example, simultaneously, or in parallel.

In more detail, at step 810 a refractive assessment may be performed. The refractive assessment may be an automated assessment performed by an autorefractor or the assessment may be a manual assessment using a phoropter. In either case, the result of the assessment is a determination of the refractive characteristic of the patient's eye. The characteristics include the sphere correction for myopia or hyperopia, the cylinder correction for astigmatism and the orientation of the axis of the cylinder for correcting the astigmatism. In some embodiments, at step 810, a refractive prescription or the results of a previously performed refractive assessment may be received.

TABLE 1

| Refractive Assessment | | | |
|---|---|---|---|
| | Sphere (D) | Cylinder (D) | Axis (degrees) |
| Right Eye (OD) | −1 | −2 | 90 |
| Left Eye (OS) | −1 | −2 | 90 |

Table 1 shows the results of an example refractive assessment for a patient, in accordance with some embodiments. The assessment shows that the patient is 1 Diopter ("D") myopic with a −2 Diopter of astigmatism. With cylindrical correction for astigmatism, a cylindrical lens is used with a zero-power axis extending along the axis of the cylinder, and the optical power of the cylindrical lens is oriented 90 degrees to the axis of the cylinder. The axis of the cylinder is measured counterclockwise from the horizontal in both eyes, as is known to one of ordinary skill in the art of optometry or ophthalmology.

With the example axis of −2 D of correcting cylinder arranged with a cylinder axis at 90 degrees, the optical power of the cylinder is located along a meridian at 180 degrees, so as to correct a steep meridian of the cornea oriented at 180 degrees. In the present example, the cornea is more steeply curved (a steeper meridian) along a mesial-lateral direction and less steeply curved, or flatter, (a flatter meridian) along a superior-inferior direction.

Although reference is made to cylinder with minus "-" optical power, the refraction can be provided with plus cylindrical optical power as will be apparent to one of ordinary skill in the art. With the example refraction above, the refraction with positive cylinder notation will be −3 (Sphere)+2 (Cylinder)×180 (degrees).

Although reference is made to the use of refractive error, a corneal topography system can be used to determine the corneal astigmatism of the eye and the corresponding steeper and flatter meridians of the cornea, in order to determine the astigmatic axes of the eye and to provide the stimulation to the retina in relation to the astigmatic axes of the cornea of the eye.

Although reference is made to treatment in relation to an astigmatic axis, the astigmatic axis may comprise a flatter axes or a steeper axis. In some embodiments, the astigmatic axis corresponds to a cylinder axis with positive cylinder notation. Alternatively, the astigmatic axis corresponds to a cylinder axis with negative cylinder notation. Also, the axis of the cylinder may correspond to the flat meridian of a cylindrical lens, or a curved meridian of the cylindrical lens such as a curved meridian perpendicular to the flat meridian.

Once the refractive error of the patient is known, the process may proceed to one or both of steps 820 and 830, and the orientation of one or more stimuli with respect to the axes determined.

At step 820 the astigmatic errors may be corrected by stimulating a change in the choroidal thickness of the eye along the meridian. In the example provided in Table 1, the patient's eye may be stimulated in relation to the axis of the patient's astigmatism. In some embodiments, in order to correct the cylindrical refractive error, the light stimulus as described herein is provided on either side of the 90-degree axis to stimulate increased choroidal thickness of the retina of the eye, on either side of, the 90-axis, as compared to the choroidal thickness of the retina of the eye at non-stimulated locations. A change in the choroidal thickness of the eye may result in a decreased growth of the sclera in the stimulated locations as compared to the unstimulated or lesser stimulated locations. In some embodiments, the stimulus such as defocused image is projected at an outer portion of the retina toward the periphery of the retina, for example within a range from 15 degrees to 40 degrees eccentric to the fovea and can be within a range from 20 degrees to 30 degrees eccentric to the fovea.

The increased thickness of the choroid and associated decrease in scleral growth can be provided by any suitable approach. In some embodiments, differential changes in choroidal thickness provide differential changes in scleral length, which provide changes in the astigmatism of the eye. A change in the choroidal thickness of the eye may result in a decreased growth of the sclera in the stimulated (or greater stimulated) locations as compared to the unstimulated (or lesser stimulated locations), so as to provide different growth of the sclera corresponding to the different astigmatic meridians of the cornea.

The stimulus locations on the retina and associated changes to the choroid and retina can be referenced with respect to the steeper and flatter meridians of the cornea. The locations of the eye corresponding to the steeper meridian may comprise locations of the eye corresponding to a plane defined by the steeper meridian of the cornea extending from the cornea and through the sclera and retina of the eye. The locations of the eye corresponding to the flatter meridian of the cornea may comprise locations of the eye corresponding to a plane defined by the flatter meridian of the cornea extending from the cornea and through the sclera and retina of the eye.

Without being bound by any particular theory, the differential changes in choroidal thickness and scleral length to treat astigmatism can be provided by alternative mechanisms. In some embodiments, the stimulus is provided at locations corresponding to the steeper meridian of the cornea, so as to decrease growth of the eye at locations corresponding to the steeper meridian and decrease astigmatism by decreasing growth of the sclera at locations corresponding to the steeper meridian (steeper meridian stimulation, "SMS"). In alternative embodiments, the stimulus is provided at locations corresponding to the flatter meridian of the cornea (flatter meridian stimulation, "FMS"), so as to decrease growth of the eye at locations corresponding to the flatter meridian and decrease astigmatism by decreasing growth of the sclera at locations corresponding to the flatter meridian. With the embodiments of the FMS approach, the increased growth of the sclera along the steeper meridian decreases tension to the cornea and relaxes the cornea along the steeper meridian so as to flatten the steeper meridian and decrease astigmatism. A person of ordinary skill in the art can conduct experiments to determine which of these alternative approaches provides better results without undue experimentation, for example by performing a clinical trial in accordance with the present disclosure.

In some embodiments, the stimulus is configured to provide differential changes in axial length of the eye to decrease the astigmatism. In some SMS embodiments, in order to correct the cylindrical refractive error, the light stimulus is provided at locations eccentric to the fovea corresponding to the steep meridian of the cornea to stimulate increased choroidal thickness and decrease growth of the sclera at locations corresponding to the steep meridian, as compared to the growth of the sclera at locations corresponding to the flatter meridian, so as to provide differential changes in axial length of the eye to decrease the astigmatism. In some embodiments, the stimulus is configured to provide differential changes in axial length of the eye to decrease the astigmatism. In some FMS embodiments, in order to correct the cylindrical refractive error, the light stimulus is provided at locations eccentric to the fovea corresponding to the flatter meridian of the cornea to stimulate increased choroidal thickness and decrease growth of the sclera at locations corresponding to the flatter meridian, as compared to the growth of the sclera at locations corresponding to the steeper meridian, so as to provide differential changes in axial length of the eye to decrease the astigmatism with relaxation of the cornea, for example.

For astigmatism correction, the focus along the meridian of the astigmatism may vary by about between 1.5-2.5 mm behind of the peripheral retina (about 2.0 D to 5.0 D, for example 2.0 D to 4.0 D, or preferably 2.5 D to 3.5 D, for example) to approximately 1.5-2.5 mm in front of the peripheral retina (about −2.0 D to −5.0 D, for example −2.0 D to −4.0 D, or preferably −2.5 D to −3.5 D, for example). In some embodiments, the stimulation is a pair of 2.0-5.0 D myopically defocused images at the retinal periphery, along the astigmatic meridian, while maintaining central vision. In some embodiments, central vision comprises of a field of view of +/−12.5 degrees, covering the macula, while foveal vision used for fixation has a field of view of +/−2.0 degrees.

Although in the example discussed above, defocused images provided at a defocus corresponding to the patient's astigmatic refractive error, in some embodiments, the defocus may be greater than the patient's refractive error. For example, a −3 Diopter defocused image may be used to stimulate the retina of a patient with a −2 Diopter astigmatism.

Devices and systems disclosed herein may be used to provide the desired stimulation. The devices are configured to provide one or more stimuli on the retina that falls outside the fovea, e.g. outside the macula, along the astigmatic meridian. The stimulation can be configured to promote a change in one or more of the axial length or choroidal thickness of the eye. The stimulus may comprise a still image or a be dynamic, for example with a refresh rate, for example within a range from 10 Hz to 200 Hz. The light may comprise monochromatic or polychromatic light. The one or more images can be configured in many ways with an image structure corresponding to information or content of the image associated with spatial frequencies. In some embodiments, the one or more images comprises a spatial frequency within a range from 1 cycle per degree to 180 cycles per degree, and a contrast within a range 99.9% to 2.5%, for example. The projected image can be projected on to the retina with an eccentricity in relation to the fovea, and the eccentricity can be within a range from 5 degrees to 40 degrees, for example. The projected image may cover a portion of the retina along the astigmatic meridian within the specified range of eccentricity, for example the projected image may be an annulus sector or arc over a minor arc length that is mirrored about a meridian 90-degrees to the astigmatic meridian. The arc length may be less than 90 degrees, less than 60 degrees, less than 45 degrees, less than 30 degrees, less than 15 degrees, less than 10 degrees, less than 5 degrees. Alternatively or in combination, the arc length may be within a range from 1 degree to 45 degrees, or within a range from 10 degrees to 35 degrees, for example. Although reference is made to an arc length, the stimulus can be configured in many ways.

In some embodiments, a single light source or group of light sources may illuminate and thereby stimulate the retina with a spot or spots in relation to the astigmatic meridian, for example along the astigmatic meridian. For example, a single light source may provide a 2 Diopter myopically defocused spot on either side of the steeper meridian, or on the flatter meridian, depending on the desired change in astigmatism. The spots may be circular with a diameter as discussed herein. In some embodiments, the stimulation is provided by light emitted by a micro-display, as discussed herein. The retinal stimulation may be applied using a light projection system or projection unit, as described herein.

In some embodiments, a plurality of light sources such as pixels of micro-displays may illuminate and thereby stimulate the retina with an image or images corresponding to steeper meridian or the flatter meridian, as discussed herein. For example, a single micro-display may provide a 2 Diopter myopically defocused image on either side of the flatter meridian. Alternatively, a single micro-display may provide a 2 Diopter myopically defocused image on either side of the steeper meridian. The images may be circular or may be of other shapes, as discussed herein. The retinal stimulation may be applied using a light projection system or projection unit.

The stimulation may be continuous or periodic or aperiodic. When periodic, the stimulation may persist for a duration within a range 1 sec to 24 hours. The stimulation may be applied when the subject is awake or asleep and combinations thereof.

Stimulation of the patient's eye to correct astigmatism may continue until the cylindrical error of the patient's eye is corrected. In the example above, the astigmatic correction may be applied to reduce the −2 Diopter astigmatism to 0.

In some embodiments, after the astigmatism of the patient's eye is corrected, the process 800 may proceed to step 830 where spherical refractive error of the patient's eye is corrected. In the example shown in Table 1, the spherical refractive error of the patient's eyes is −1 Diopter. To correct this spherical refractive error light from light sources of the projection units are focused by one or more projection optics, as described herein.

At step 830 the spherical errors may be corrected by stimulating a change in the axial length of the eye eccentric to the fovea. In some embodiments, in order to correct the spherical refractive error, stimuli are provided through both of the meridians of the cornea to stimulate growth of the choroidal thickness of the eye and a change in the axial length of the eye corresponding to a change in spherical refractive error. In some embodiments, the stimulus such as a defocused image is projected at an outer portion of the retina toward the periphery of the retina, for example within a range from 15 degrees to 40 degrees eccentric to the fovea and can be within a range from 20 degrees to 30 degrees.

Devices and systems disclosed herein may be used to provide the desired stimulation. The devices are configured to provide a stimulus on the retina eccentric to the fovea. The spherical stimulation can be configured to promote a change in the axial length or choroidal thickness of the eye. The stimulus may comprise a still stimulus or be dynamic, for example with a refresh rate as discussed herein. The light of the image may comprise monochromatic or polychromatic light. The one or more images can be configured in many ways with an image structure corresponding to information or content of the image associated with spatial frequencies. In some embodiments, the one or more images comprises a spatial frequency within a range from 1 cycle per degree to 180 cycles per degree or 1 cycle per degree to 60 cycles per degree, and a contrast within a range 99.9% to 2.5%, for example. The projected image can be projected on to the retina with an eccentricity in relation to the fovea, and the eccentricity can be within a range from 5 degrees to 40 degrees. The projected image may cover a portion of the retina within the specified range of eccentricity, for example the projected image may be an annular shape extending within a range from 5 degrees to 40 degrees, from 15 degrees to 40 degrees, or from 20 degrees to 30 degrees eccentric to the fovea.

Stimulation of the patient's eye to correct spherical refractive error may continue until the cylindrical error of the patient's eye is corrected. In the example above, the spherical correction may be applied to reduce the −1 Diopter spherical refractive to approximately 0.

While the above process describes the actions of step 820 occurring before the actions of step 830, in some embodiments, the actions of step 830 may occur before the actions of step 820. For example, the spherical refractive error of the eye may be corrected from −1 to about 0 before the astigmatic refractive error is corrected from −2 to about 0. In some embodiments, the actions of steps 820 and 830 may be interleaved. For example, a partial astigmatic correction from −2 to −1 may be performed according to step 820 followed by a partial spherical correction from −1 to −0.5, followed by a second partial astigmatic correction from −1 to 0 and then a second partial spherical correction from −0.5 to 0. Although the partial corrections are described in four interleaved steps, any number of interleaved steps may be used to correct the refractive errors of the patient.

In some embodiments, step 820 and step 830 may be combined and the spherical and astigmatic refractive errors of the eye may be corrected at the same time. For example, the eye may be stimulated about the steep meridian along which the patient's astigmatism occurs at the same time the eye is stimulated through the flatter meridian eccentric to and about the fovea.

In some embodiments, the stimulation provided to the retina for simultaneous correction of the spherical and astigmatic refractive errors may be different than that provided during separate correction steps while the intensity of the light or image is the same for both regions. For example, in some embodiments of simultaneous correction the refractive correction may be additive to the spherical correction in the areas stimulated for astigmatic correction.

In some embodiments, spherical and astigmatic refractive errors may be corrected by varying the intensity of the light or image with keeping the amount of defocus the same. For example, a stimulus such as an image may be provided to the retina at a −2 Diopter defocus eccentric to the fovea to stimulate growth of the choroidal thickness of the eye and a change in the axial length of the eye about in the peripheral area around the fovea. However, to treat the spherical errors and astigmatic errors at the same time, the light may be provided at two or more intensities or two or more different intervals. For example, the intensity of the stimulating light or the image for treating the astigmatic regions may be provided at a first intensity while the intensity of the stimulating light or images in the areas for treating only the spherical errors may be at a second intensity. The first intensity may be greater than the second intensity to stimulate growth of the choroidal thickness of the eye and a change in the growth of the sclera along the steeper meridian of the astigmatism at a rate lower than the rate of growth of the sclera at locations way from the locations corresponding to the flatter meridian.

In some embodiments, the duration of the stimulation may be varied. For example, stimulation may be applied on a daily or other time-based basis. In such embodiments, a patent with different amounts of astigmatic and spherical refractive errors may have different time-based stimulation to treat the errors. For example, a patient with a spherical and cylindrical refractive error in an eye may have astigmatic stimulation for four hours a day and spherical stimulation for two hours a day.

In some embodiments, the simultaneous treatment of the astigmatic and spherical refractive errors of the eye may vary in one or more of intensity, defocus, and periodic stimulation. For example, the spherical refractive error correction may be a −1 Diopter defocused image or light at a first intensity eccentric to the fovea in areas not stimulated by the refractive stimulation while the astigmatic refractive error correction may be −3 Diopters along the steeper meridian at a second intensity. The first intensity may be great than or less than the second intensity. The difference in the intensity may be varied based on the amount of defocus. For example, less defocus may be used in combination with greater intensity of light and more time-based periodic treatment or more defocus may be used in combination with lesser intensity of light and less time-based periodic treatment.

Figure 9A:
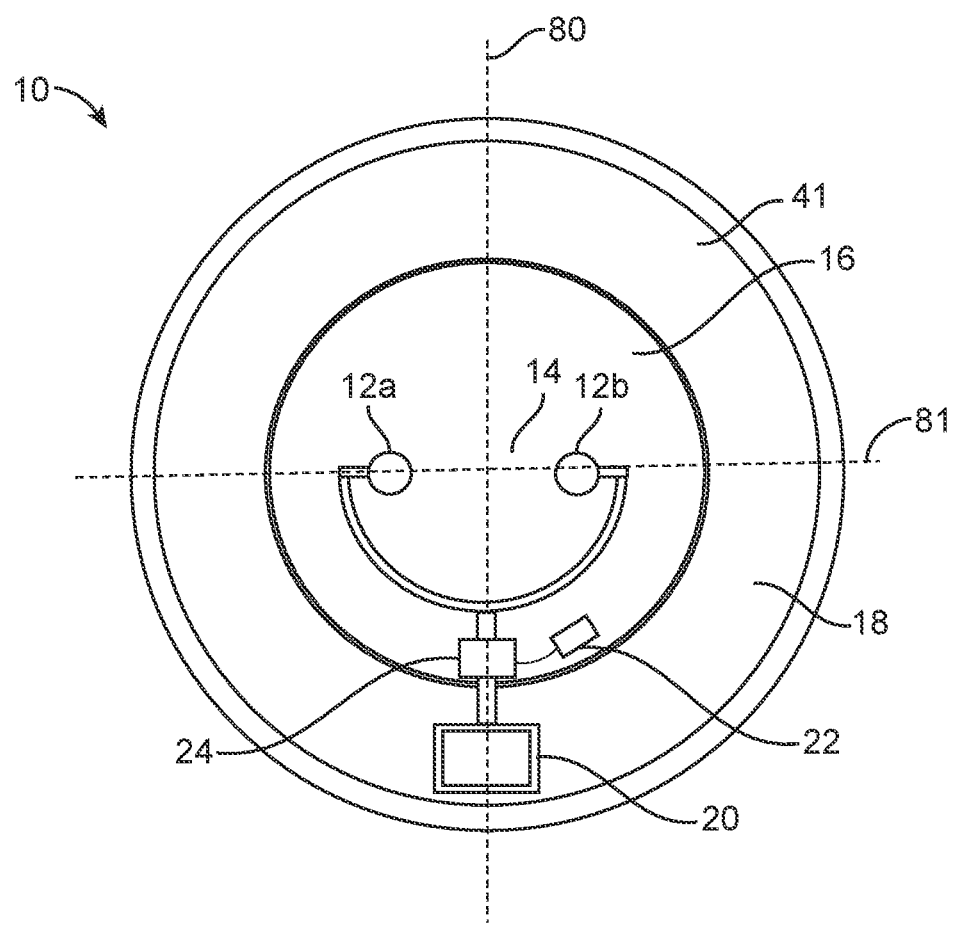
FIG. 9A shows soft contact lens with embedded light sources, optics and electronics for projecting images with defocus on the periphery of the retina of a wearer, in accordance with some embodiments.
Figure 9B:
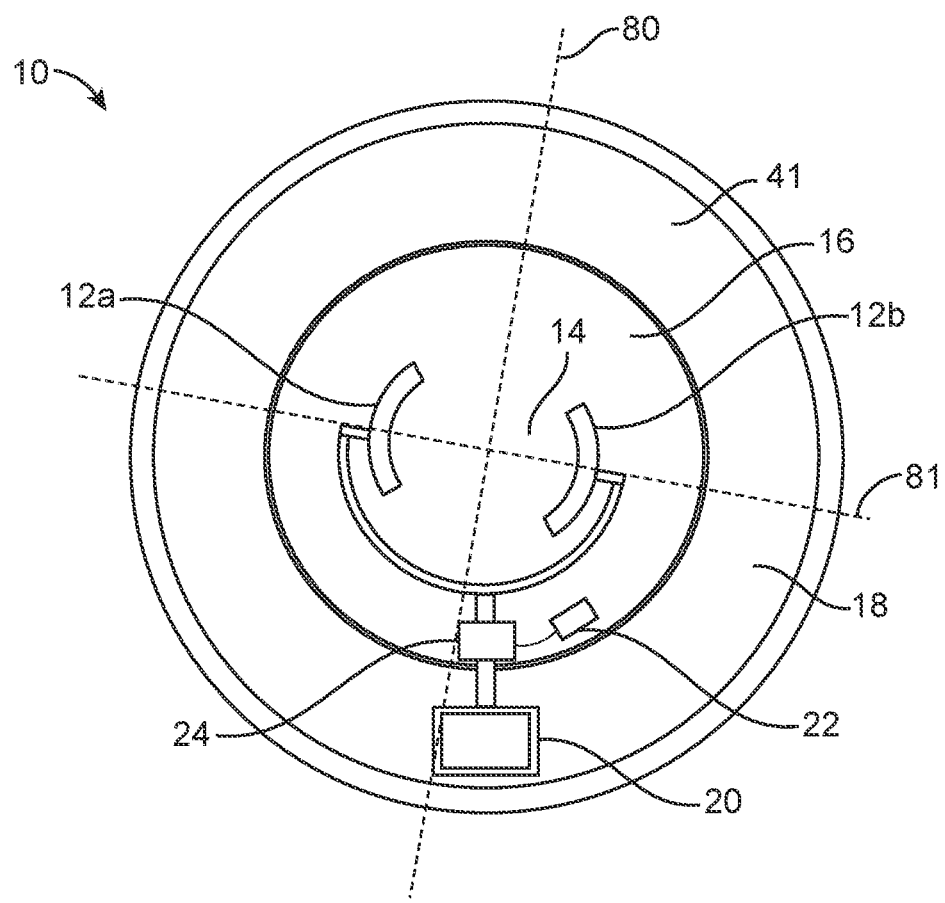
FIG. 9B shows soft contact lens with embedded light sources, optics and electronics for projecting images with defocus on the periphery of the retina of a wearer, in accordance with some embodiments.

FIGS. 9A and 9B depict a contact lenses 10 configured to provide a stimulus to treat astigmatism, such as a defocused image projected on the retina at locations corresponding to a meridian of astigmatism of a patient and away from the central field of vision, e.g. away from the macula, in order to stimulate a change in choroidal thickness. Although reference is made to a contact lens, the lens 10 may comprise a lens of one or more of a projector, a spectacle lens, an ophthalmic equipment, a contact lens, a corneal onlay, a corneal inlay, a corneal prosthesis, or an intraocular lens. For example, the lens may comprise a spectacle lens with the light sources located in relation to the axis of astigmatism in order to provide peripheral stimulation to treat astigmatism as described herein.

The lens 10 can be configured in many ways, and may comprise one or more components of the contact lens described with reference to FIGS. 1 and 2. The lens 10 comprises an axis 80. The contact lens 10 is configured to align the axis 80 with align with an astigmatic axis of the eye, such as one or more of a refractive astigmatic axis or a meridian of the cornea as described herein. The optical zone of the contact lens may comprise an optical zone configured to correct spherical and cylindrical refractive error, e.g. a toric optical zone, which is aligned with an astigmatic axis 80. The contact lens may comprise a second astigmatic axis 81, which extends generally transverse to the first axis 80. In some embodiments, the second astigmatic axis 81 is substantially perpendicular to the first astigmatic axis for example at an angle with in a range from about 80 degrees to 100 degrees of the first astigmatic axis. In SMS embodiments, the astigmatic axis 80 corresponds to the flatter meridian of the cornea and the axis 81 corresponds to the steeper meridian of the cornea. The light sources such as projection units 12a and 12b are configured to provide a stimulus to the retina at locations corresponding to the astigmatic axes of the eye. In some embodiments, the first light source and the second light source are located on opposite sides of an astigmatic axis or meridian to treat the astigmatism with retinal stimulation at locations corresponding to a first astigmatic axis or meridian, and the light sources can be configured to provide decreased illumination at locations corresponding to a second meridian.

In some embodiments, stimulation of the eye to correct for astigmatism occurs along the astigmatic meridian. A lens such as contact lens 10 may be stabilized with respect to the eye, for example stabilized on the eye. For example, in some embodiments, the lens is stabilized on the eye to orient the lens in an inferior-superior direction. In some SMS embodiments, the lens is stabilized such that the projection units 12 are disposed (e.g. symmetrically disposed) on opposite sides of the flatter meridian of the cornea and located along the astigmatic or steep axis corresponding to the steep meridian of the cornea. In alternative embodiments (e.g. FMS embodiments), the lens is stabilized such that the projection units 12 are disposed (e.g. symmetrically disposed) on opposite sides of the steeper meridian of the cornea and located along the astigmatic or flat axis corresponding to the flatter meridian of the cornea. In some embodiments, the axis 80 comprises an axis of symmetry about which the projection units 12a, 12b are symmetrically located. While the projection units 12a, 12b can be sized and shaped in many ways, in some embodiments, the projection units comprise an arcuate shape profile corresponding to a segment of an annulus, so as to provide an annular stimulus to the retina. In some embodiments, the light from the stimulus traverses an optical axis of the eye to illuminate an arcuate region of the retina on the opposite side of the eye.

In the example discussed in Table 1, the axis of a corrective cylinder is at 90 degrees, therefore, the contact lens 10 may be stabilized in the eye such that the astigmatic axis 80 of the lens 10 substantially aligns with or is parallel to a prescribed cylinder axis, which may be the flatter meridian of the cornea and the projection units project images to locations with respect to the astigmatic meridian of the cornea, such as along the astigmatic meridian, when the lens 10 is stabilized in an inferior-superior direction.

The contact lens 10 may include a ballast or weight that is asymmetric such that gravity acts on the ballast or weight to pull it down in a direction that stabilizes the contact lens and aligns the lens and its projection unites with the astigmatic meridian. In some embodiments, the contact lens 10 may be shaped to be blink stabilized, such that the patient's natural blinking acts on the shape of the contact lens to stabilize and orientate the lens in the patient's eye. In some embodiments, other stabilization methods may be used to align the lens 10 and its astigmatic axis with the eye.

In some embodiments, the contact lens 10 may have projection units that are asymmetrical with respect to the contact lens 10. In such embodiments, the projection units on contact lens 10 may not have an axis of symmetry but may still be aligned with the eye such that the projection units 12 stimulate the eye at locations corresponding to an astigmatic meridian.

In the contact lens 10, one or more of the battery 20, PCB 24, the sensors 22 or other components of the contact lens 10 may act as a ballast for stabilizing the contact lens and aligning the stimulation with the astigmatic meridian of the eye. In the example of Table 1, the prescribed cylinder axis is 90 degrees, vertical with respect to the patient's body. As shown in FIG. 9A, the battery 20, acting as a ballast, is aligned with the axis of symmetry 80 of the contact lens to align the axis of symmetry 80 with a horizontal, 180-degree astigmatic meridian.

In some embodiments, the astigmatic cylinder correction axes may be at angles other than 90. For example, a patient may have an astigmatic cylinder correction axis 80 at 80 degrees and an axis 81 at 170 degrees. FIG. 9B shows a contact lens 10 with a ballast positioned offset from the axis of astigmatism 80 of the projection units 12, such the axis 80 aligns with an 80 degree astigmatic cylinder correction axis. In some embodiments, the shapes of the contact lens that enable blink or other types of stabilization may be offset from the axis of symmetry of the projection units such that the projection units are positioned along the astigmatic meridian when the contact lens 10 is stabilized in the patent's eye. FIG. 9B also depicts micro-displays 12 in the shape of annulus segments.

In accordance with some embodiments, a soft contact lens 10 comprises projection units as described herein.

The processor on the lens 10, may be programmed or otherwise configured with instructions to selectively illuminate the projection optics to project light to a plurality of locations on the retina to treat one or both of myopia and astigmatism. The selective illumination and accompanying stimulation and treatment may be carried out as discussed with respect to FIG. 8 and steps 820 and 830. For example, in the treatment of astigmatism, a processor in a lens such as that depicted in FIGS. 9A and 9B, may be selectively controlled to illuminate and project images onto the retina. In some embodiments, such as the contact lens shown in FIG. 2, a first group of optics, such as those arranged along the steep meridian of the cornea may be selectively illuminated to treat one or both of astigmatism and myopia at selected location of the retina along the steep meridian while a second group of optics, such as those arranged along a flatter meridian of the cornea may be selectively illuminated to treat myopia at selected locations of the retina along the flatter meridian.

Figure 10:
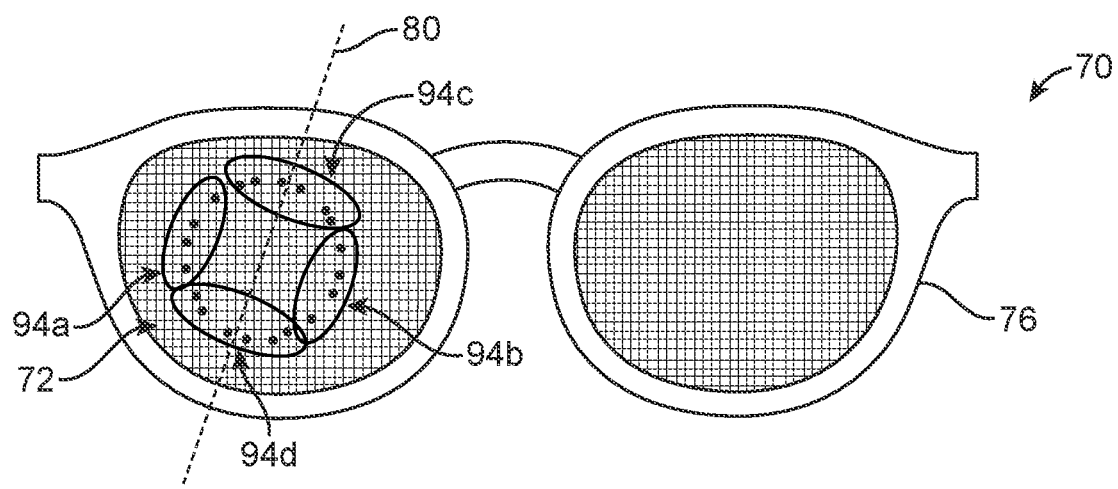
FIG. 10 shows a spectacle lens, in which groups of pixels are orientated symmetrically about an axis to treat astigmatism, in accordance with some embodiments.

FIG. 10 depicts spectacles 70 as in FIGS. 7A and 7B configured for the treatment of refractive astigmatism. The spectacles 70 comprise a first astigmatic axis 80 and a second astigmatic axis 81 as described herein. The spectacles can be configured for steep meridian stimulation (SMS) or flat meridian stimulation (FMS) as described herein. The spectacles may be programmed to provide stimuli to treat refractive error with selection of appropriate light sources under processor control, for example.

The micro display and optics can be configured in many ways to provide appropriate stimulation to outer regions of the retina toward the periphery. For example, FIG. 10 depicts four groups 94a, 94b, 94c, and 94d, of pixels 94. For a patient with refractive errors as discussed above with reference to Table 1, groups 94a and 94b may provide stimulation for the treatment of astigmatic errors. Alternatively or in combination, groups 94a, 94b, 94c, and 94d may provide stimulation for the treatment of spherical errors.

For example, in some embodiments, at step 820 in order to correct the cylindrical refractive error, light or an image is provided at a defocus on either side of the axis 80 by groups 94a and 94b to stimulate growth of the choroidal thickness of the eye and provide differential scleral growth of the eye as described herein.

In some embodiments, at step 830 in order to correct the spherical refractive error, a stimulus such as an image is provided to the retina eccentric to the fovea by groups 94a, 94b, 94c, and 94d to stimulate growth of the choroidal thickness of the eye and a decrease increases in the axial length of the eye about in the peripheral area around the fovea, as described herein above.

The stimulation to correct the cylindrical error and the spherical error may be provided separately or at the same time. For example, in some embodiments, in order to correct the cylindrical refractive error, a stimulus such as an image is provided on either side of the axis 80 by groups 94a and 94b to stimulate increases in the choroidal thickness of the eye and provide differential scleral growth, such as differential growth of sclera corresponding to the axial length of the eye. As described herein, the axis 80 may correspond to the steeper meridian of the cornea or the flatter meridian of the cornea. In some embodiments, groups 94c and 94d are activated less than groups 94a and 94b.

As discussed above with respect to FIGS. 8, 9A and 9B, the stimulation to correct astigmatic and spherical errors may be provided at different intensities, amount of defocus and at different time-based periodic treatment.

The spectacles may include one or more processors that may be programmed or otherwise configured with instructions to selectively illuminate the projection optics to project light to a plurality of location son the retina to treat one or both of myopia and astigmatism. The spectacles may comprise one or more components of the mechanical integration function referred to in FIG. 3. The selective illumination and accompanying stimulation and treatment may be carried out as discussed with respect to FIG. 8 and steps 820 and 830. For example, in the treatment of astigmatism, a processor may selectively control groups of one or more pixels to illuminate and project images onto the retina. In some embodiments, the processor may control a first group of pixels, such as those arranged along the steep meridian of the cornea to be selectively illuminated to treat one or both of astigmatism and myopia at selected location of the retina along the steep meridian while a second group of one or more pixels, such as those arranged along a flatter meridian of the cornea may be selectively illuminated to treat myopia at selected locations of the retina along the flatter meridian.

Although FIG. 10 depicts micro displays with more than one active pixel in each group 94a, 94b, 94c, and 94d, in some embodiments, each group may include a single pixel. In some embodiments, for example, for treatment of astigmatic refractive errors, only a single pixel or light source may be used for stimulation on each side of the flatter meridian, along the steeper meridian.

While the example in Table 1 includes an astigmatic refractive error at 90 degrees, in some embodiments, the refractive errors may be at other angles. FIG. 10 depicts an embodiment where a first astigmatic axis 80 is at 80 degrees, and a second astigmatic axis is a 170 degrees. In some embodiments, the groups 94a and 94b of pixels 94 are orientated symmetrically about astigmatic axis 80 to project defocused images transverse to the axis to correct the astigmatism of a patient while groups 94c and 94d may also be rotated in order to provide a stimulus such as defocused images to correct spherical errors of the eye.

In some embodiments, the intensity and duration of activated pixels are configured so as to correspond to an astigmatic axis of treatment. For example, each of the plurality of groups 94a, 94b, 94c and 94d may comprises pixels with different intensities or durations to as to compensate for different distances from astigmatic axis 80. In some embodiments, each of the plurality of groups comprises a first stimulus having a first intensity and a first duration at a first distance from the astigmatic axis 80 and a second stimulus on a second side having a second intensity and a second duration at a second distance from the astigmatic axis. In some embodiments, for each of the plurality of groups, 94a, 94b, 94c, 94d, one or more of the second intensity or the second duration is different from one or more of the first intensity or the first direction to compensate for the first difference being different from the second distance.

This has the advantage of improving the accuracy of treatment and allowing a decreased pixel resolution.

For example, the eye glass prescription may comprise a −2.00 D cylinder with a prescription astigmatic axis with an angle of 75 degrees. The optical power of such a cylinder is located 90 degrees from the prescription axis, e.g. at 165 degrees. The stimuli can be located at 180 degrees and 150 degrees, respectively, in order to treat at 165 degrees, for example. If both of those stimuli provide equal values of intensity and duration the vector would be on the minus 2 power meridian of 165 degrees, which corresponds to the prescription of −2.00×75 degrees. Alternatively, one or more of the intensity or duration of the stimuli can be adjusted to provide treatment corresponding to different axes, e.g. 164 degrees. For example, a first stimulus closer to an axis may comprise one or more of an intensity or a duration that is less than the intensity or duration of a second stimulus that is farther from the axis.

Although reference is made to projecting images onto the retina to treat astigmatism, the stimulus can be provided in many ways. For example, the stimulus can be provided with illumination sources that provide light to the retina without projecting an image into the eye. In some embodiments, the stimulus comprises scattered light passed through a scattering medium. The light scattering medium can be located in relation to the lens similar to the locations described herein with reference to the projection units. Alternatively, the stimulus may comprise a pattern shown a display to provide a stimulus to treat astigmatism, for example an arcuate pattern on a display, similar to the arcuate projection units 12a and 12b as described herein.

The amounts and location of illumination on outer locations of the retina to provide astigmatism correction can be determined by one of ordinary skill in the art without undue experimentation in accordance with the teachings disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. An apparatus to treat an astigmatism of an eye with retinal stimulation of the eye, the apparatus comprising: a light source configured to provide a stimulus to a retina of the eye, wherein the stimulus is configured to be aligned with respect to an astigmatic axis of the eye to treat the astigmatism of the eye.

Clause 2. The apparatus of clause 1, wherein the stimulus comprises a first light stimulus on a first side of the astigmatic axis and a second light stimulus on a second side of the astigmatic axis.

Clause 3. The apparatus of clause 2, wherein the first stimulus comprises a first intensity and a first duration at a first distance from the astigmatic axis and the second stimulus on the second side comprises a second intensity and a second duration at a second distance from the astigmatic axis and wherein one or more of the second intensity or the second duration is different from one or more of the first intensity or the first direction to compensate for the first difference being different from the second distance.

Clause 4. The apparatus of clause 2, wherein the eye comprises a second astigmatic axis, and wherein the first light stimulus and the second light stimulus are arranged to illuminate the retina along the second astigmatic axis to decrease astigmatism along the first axis.

Clause 5. The apparatus of clause 1, wherein the light source is configured to illuminate the retina with a first light stimulus on a first side of the astigmatic axis and a second light stimulus on a second side of the astigmatic axis.

Clause 6. The apparatus of clause 5, wherein the light source is configured to inhibit illumination of a macula with the first stimulus and the second stimulus.

Clause 7. The apparatus of clause 1, wherein the light source is arranged to provide light to a first region of peripheral retina outside a macula and a second region of peripheral retina outside the macula, the second region opposite the first region with the macula of the retina located between the first region and the second region.

Clause 8. The apparatus of clause 7, wherein the retina comprises a third region between the first region and the second region on a first side of the macula and a fourth region between the first region and the second region on a second side of the macula and wherein the light source is configured to provide greater amounts of light to the first region and the second region than to the third region and the fourth region.

Clause 9. The apparatus of clause 8, wherein each of the four regions comprises a quadrant of the retina, the first region corresponding to a first quadrant, the second region corresponding to a second quadrant, the third region corresponding to a third quadrant, the fourth region corresponding to a fourth quadrant.

Clause 10. The apparatus of clause 1, further comprising: a lens comprising an optical zone for the eye to view an object; and a plurality of optics arranged around the optical zone to project a plurality of images anterior to the retina of the eye at a plurality of locations outside one or more of a fovea or a macula of the eye, the plurality of optics arranged with respect to an astigmatic meridian of the eye.

Clause 11. The apparatus of clause 10, further comprising a processor coupled to the plurality of optics, the processor configured with instructions to project light to the plurality of locations.

Clause 12. The apparatus of clause 11, wherein the plurality of optics is arranged to treat astigmatism with a first plurality of optics and to treat myopia and astigmatism with a second plurality of optics and the first plurality of optics and wherein the processor is configured with instructions to illuminate the first plurality of optics to treat the astigmatism and to illuminate the first plurality of optics and second plurality of optics to treat the myopia.

Clause 13. The apparatus of clause 12, wherein the first plurality of optics is configured to deliver an amount of light to treat the astigmatism corresponding to a steep meridian of a cornea and wherein the second plurality of optics is configured to treat myopia corresponding to a flatter meridian of the cornea located 90 degrees from the steep meridian of the cornea.

Clause 14. The apparatus of clause 13, wherein the first plurality of optics is configured to pass through a steeper region of the cornea than the second plurality of optics.

Clause 15. The apparatus of clause 13, wherein the first plurality of optics is configured to pass through a flatter region of the cornea than the second plurality of optics.

Clause 16. The apparatus of clause 14, wherein each the first plurality of optics and the second plurality of optics is configured to transmit light across an optical axis of the lens to project an image anterior to the retina on an opposite side of the optical axis.

Clause 17. The apparatus of clause 12, wherein the processor is configured to treat the myopia and astigmatism sequentially.

Clause 18. The apparatus of clause 12, wherein the processor is configured with instructions to selectively illuminate each of the first plurality of optics and the second plurality of optics.

Clause 19. The apparatus of clause 12, wherein the processor is programmable with instructions to selectively illuminate the second plurality of optics in relation to an astigmatic meridian on the eye and wherein the lens is stabilized when placed in front of the eye.

Clause 20. The apparatus of clause 10, wherein the astigmatic meridian corresponds to a meridian of a cornea having a curvature steeper than a curvature of a flatter meridian of the cornea, and wherein the plurality of optics is configured to decrease scleral growth at locations of the sclera corresponding to the steeper meridians to decrease the astigmatism of the eye.

Clause 21. The apparatus of clause 20, wherein a steep meridian of the cornea corresponds to a line along the retina and wherein the line extends through the plurality of locations.

Clause 22. The apparatus of clause 21, wherein the plurality of optics is configured to decrease growth of the sclera at locations corresponding to the steep meridian in relation to growth of the sclera at locations away from the locations corresponding to the steep meridian.

Clause 23. The apparatus of clause 20, wherein the flatter meridian of the cornea corresponds to a line along the retina and wherein the line extends through the plurality of locations.

Clause 24. The apparatus of clause 23, wherein the plurality of optics is configured to decrease growth of the sclera at locations corresponding to the flatter meridian in relation to growth of the sclera at locations away from the locations corresponding to the flatter meridian.

Clause 25. The apparatus of clause 10, wherein the astigmatic meridian corresponds to a meridian of a cornea having a curvature steeper than a curvature of a flatter meridian of the cornea, and wherein the plurality of optics is configured to decrease scleral growth at locations of the sclera corresponding to the flatter meridians to decrease the astigmatism of the eye.

Clause 26. The apparatus of clause 10, wherein the plurality of optics is configured to promote a change in one or more of an axial length or a choroidal thickness of the eye to treat the astigmatism.

Clause 27. The apparatus of clause 10, wherein the plurality of optics is configured to transmit light across an optical axis of the lens to project an image anterior to the retina on an opposite side of the optical axis.

Clause 28. The apparatus of clause 10, wherein the astigmatic meridian of the eye comprises a steep meridian of a cornea of the eye and wherein the plurality of locations of the retina corresponds to the steep meridian.

Clause 29. The apparatus of clause 28, wherein an optical axis of the lens extends from the object through the optical zone to a fovea of the eye and wherein light from the plurality of optics traverses the optical axis and extends to the plurality of locations.

Clause 30. The apparatus of clause 29, wherein light from each of the plurality of optics extends to a corresponding location on the retina and traverses the optical axis.

Clause 31. The apparatus of clause 10, wherein the lens comprises stabilization to orient the lens in an inferior superior direction along the eye, and wherein the plurality of optics is arranged to direct the light with respect to the astigmatic meridian with the lens stabilized on the eye in the inferior superior direction.

Clause 32. The apparatus of clause 31, wherein the lens comprises a contact lens and wherein the contact lens comprises contact lens stabilization.

Clause 33. The apparatus of clause 31, wherein the lens comprises a spectacle lens and wherein the spectacle lens is supported with an eyeglass frame.

Clause 34. The apparatus of clause 10, wherein each of the plurality of optics is configured to project an image at a location anterior or posterior to a corresponding retinal location to treat the astigmatism.

Clause 35. The apparatus of clause 10, wherein each of the plurality of optics is configured to project an image anterior to the retina at a corresponding retinal location.

Clause 36. The apparatus of clause 35, wherein the lens comprises a spectacle lens and wherein the plurality of optics has been adjusted to reduce an effect of astigmatism on a location of image formation anterior to the retina.

Clause 37. The apparatus of clause 10, wherein the lens comprises a spectacle lens and wherein an eye position sensor is configured to adjust the plurality of optics reduce movement of the plurality of locations on the retina in response to eye movement.

Clause 38. The apparatus of clause 10, wherein the lens comprises one or more of a plano lens, a spherical correction lens, an astigmatic correction lens, or prism correction lens.

Clause 39. A method of treating an eye, the method comprising: providing a stimulus to a retina of the eye, wherein the stimulus is aligned with respect to an astigmatic axis of the eye to treat an astigmatism of the eye.

Clause 40. The method of clause 39, wherein the stimulus comprises a first light stimulus on a first side of the astigmatic axis and a second light stimulus on a second side of the astigmatic axis.

Clause 41. The method of clause 40, wherein the first stimulus comprises a first intensity and a first duration at a first distance from the astigmatic axis and the second stimulus on the second side comprises a second intensity and a second duration at a second distance from the astigmatic axis and wherein one or more of the second intensity or the second duration is different from one or more of the first intensity or the first direction to compensate for the first difference being different from the second distance.

Clause 42. The method of clause 40, wherein the eye comprises a second astigmatic axis, and wherein the first light stimulus and the second light stimulus are arranged along the second astigmatic axis to decrease astigmatism along the first axis.

Clause 43. The method of clause 39, wherein the stimulus is configured to inhibit illumination of a macula with the first stimulus and the second stimulus.

Clause 44. The method of clause 39, wherein the stimulus is arranged to provide light to a first region of peripheral retina outside a macula and a second region of peripheral retina outside the macula, the second region opposite the first region with the macula of the retina located between the first region and the second region.

Clause 45. The method of clause 44, wherein the retina comprises a third region between the first region and the second region on a first side of the macula and a fourth region between the first region and the second region on a second side of the macula and wherein the stimulus provides greater amounts of light to the first region and the second region than to the third region and the fourth region.

Clause 46. The method of clause 45, wherein each of the four regions comprises a quadrant of the retina, the first region corresponding to a first quadrant, the second region corresponding to a second quadrant, the third region corresponding to a third quadrant, the fourth region corresponding to a fourth quadrant.

Clause 47. The method or apparatus of any one of the preceding clauses wherein the astigmatic axis corresponds to a cylinder axis with plus cylinder notation.

Clause 48. The method or apparatus of any one of the preceding clauses wherein the astigmatic axis corresponds to a cylinder axis with minus cylinder notation.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus to treat an astigmatism of an eye with retinal stimulation of the eye, the apparatus comprising:

a lens having an astigmatic axis;

a light source comprising a first light source to provide a first stimulus and a second light source to provide a second stimulus to a retina of the eye, wherein the first light source is aligned with respect to the astigmatic axis of the lens and the second light source is aligned with respect to the astigmatic axis of the lens to treat the astigmatism of the eye; and a processor coupled to the light source, the processor configured with instructions to cause the first light source to provide the first stimulus aligned with respect to the astigmatic axis at a first intensity and the second light source to provide the second stimulus aligned with respect to the astigmatic axis at a second intensity.

2. The apparatus of claim 1, wherein the first light source provides the first stimulus on a first side of the astigmatic axis of the lens and the second light sources provides the second stimulus on a second side of the astigmatic axis of the lens.

3. The apparatus of claim 2, wherein the first stimulus on the first side comprises a first duration at a first distance from the astigmatic axis and the second stimulus on the second side comprises a second duration at a second distance from the astigmatic axis and wherein one or more of the second intensity or the second duration is different from one or more of the first intensity or the first distance.

4. The apparatus of claim 2, wherein the lens comprises a second astigmatic axis transverse to the astigmatic axis, and wherein the first stimulus and the second stimulus are arranged to illuminate the retina along the second astigmatic axis to decrease astigmatism of the eye along the astigmatic axis.

5. The apparatus of claim 1, wherein the first light source is configured to illuminate the retina with the first light stimulus on a first side of the astigmatic axis and the second light source is configured to illuminate the retina with the second stimulus on a second side of the astigmatic axis.

6. The apparatus of claim 5, wherein the first light source and the second light source are configured to inhibit illumination of a macula with the first light stimulus and the second light stimulus.

7. The apparatus of claim 1, wherein the first light source and the second light source are arranged to provide the first stimulus to a first region of the peripheral retina outside a macula and to provide the second stimulus to a second region of peripheral retina outside the macula, the second region opposite the first region with the macula of the retina located between the first region and the second region.

8. The apparatus of claim 7, wherein the retina comprises a third region between the first region and the second region on a first side of the macula and a fourth region between the first region and the second region on a second side of the macula and wherein the first light source and the second light source are configured to provide greater amounts of light to the first region and the second region than to the third region and the fourth region.

9. The apparatus of claim 8, wherein each of the four regions comprises a quadrant of the retina, the first region corresponding to a first quadrant, the second region corresponding to a second quadrant, the third region corresponding to a third quadrant, the fourth region corresponding to a fourth quadrant.

10. The apparatus of claim 1, wherein:

the lens comprises an optical zone for the eye to view an object and wherein a plurality of optics coupled to a plurality of light sources is arranged around the optical zone to project a plurality of images anterior to the retina of the eye at a plurality of locations outside one or more of a fovea or a macula of the eye, the plurality of optics arranged with respect to the astigmatic axis of the lens, the astigmatic axis of the lens corresponding to an astigmatic meridian of the eye.

11. The apparatus of claim 10, wherein the plurality of optics is arranged with respect to the astigmatic axis of the lens to treat the astigmatism with a first plurality of optics coupled to a first plurality of light sources and to treat a myopia of the eye and the astigmatism with a second plurality of optics coupled to a second plurality of light sources and the first plurality of optics coupled to the first plurality of light sources and wherein the processor is configured with instructions to illuminate the first plurality of optics with the first plurality of light sources to treat the astigmatism and to illuminate the first plurality of optics with the first plurality of light sources and the second plurality of optics coupled to the second plurality of light sources to treat the myopia.

12. The apparatus of claim 11, wherein the first plurality of optics is arranged with respect to the astigmatic axis of the lens to deliver an amount of light to treat the astigmatism corresponding to a steep meridian of a cornea and wherein the second plurality of optics is arranged with respect to the astigmatic axis of the lens to treat the myopia corresponding to a flatter meridian of the cornea transverse to the steep meridian of the cornea.

13. The apparatus of claim 12, wherein the first plurality of optics is configured to pass light through a steeper region of the cornea than the second plurality of optics.

14. The apparatus of claim 13, wherein each the first plurality of optics and the second plurality of optics is configured to transmit light across an optical axis of the lens to project an image anterior to the retina on an opposite side of the optical axis.

15. The apparatus of claim 12, wherein the first plurality of optics is configured to pass light through a flatter region of the cornea than the second plurality of optics.

16. The apparatus of claim 11, wherein the processor is configured to treat the myopia and the astigmatism sequentially.

17. The apparatus of claim 11, wherein the processor is configured with instructions to selectively illuminate each of the first plurality of optics and the second plurality of optics.

18. The apparatus of claim 11, wherein the processor is programmable with instructions to selectively illuminate the second plurality of optics in relation to the astigmatic axis of the lens, the astigmatic axis of the lens corresponding to an astigmatic meridian on the eye and wherein the lens is stabilized when placed in front of the eye.

19. The apparatus of claim 10, wherein the astigmatic meridian corresponds to a steeper meridian of a cornea having a curvature steeper than a curvature of a flatter meridian of the cornea, and wherein the plurality of optics is configured to decrease a growth of a sclera at locations of the sclera corresponding to the steeper meridian to decrease the astigmatism of the eye.

\* \* \* \* \*